(12) United States Patent
Ishiyama et al.

(10) Patent No.: US 9,543,526 B2
(45) Date of Patent: Jan. 10, 2017

(54) NITROGEN-CONTAINING AROMATIC COMPOUNDS AND ORGANIC ELECTROLUMINESCENT DEVICE

(75) Inventors: Takaya Ishiyama, Kitakyushu (JP); Hiroyuki Hayashida, Kitakyushu (JP); Mitsuru Sakai, Kitakyushu (JP); Masashi Niina, Kitakyushu (JP); Kazuto Shiraishi, Kitakyushu (JP); Kazuaki Yoshimura, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 631 days.

(21) Appl. No.: 14/004,991

(22) PCT Filed: Feb. 9, 2012

(86) PCT No.: PCT/JP2012/052937
§ 371 (c)(1),
(2), (4) Date: Sep. 13, 2013

(87) PCT Pub. No.: WO2012/124412
PCT Pub. Date: Sep. 20, 2012

(65) Prior Publication Data
US 2014/0001458 A1    Jan. 2, 2014

(30) Foreign Application Priority Data
Mar. 16, 2011   (JP) ................................ 2011-057753

(51) Int. Cl.
| | | |
|---|---|---|
| H01L 51/54 | (2006.01) |
| C09K 11/06 | (2006.01) |
| H01L 51/00 | (2006.01) |
| C07D 471/14 | (2006.01) |
| C07D 491/147 | (2006.01) |
| C07D 495/14 | (2006.01) |
| H01L 51/50 | (2006.01) |

(52) U.S. Cl.
CPC ......... *H01L 51/0065* (2013.01); *C07D 471/14* (2013.01); *C07D 491/147* (2013.01); *C07D 495/14* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *H01L 51/0037* (2013.01); *H01L 51/0081* (2013.01); *H01L 51/0085* (2013.01); *H01L 51/5016* (2013.01); *H01L 51/5056* (2013.01)

(58) Field of Classification Search
None
See application file for complete search history.

(56) References Cited

U.S. PATENT DOCUMENTS

| | | |
|---|---|---|
| 2002/0034655 A1 | 3/2002 | Watanabe et al. |
| 2004/0137271 A1 | 7/2004 | Sohn et al. |
| 2006/0214155 A1 | 9/2006 | Ong et al. |
| 2008/0220285 A1 | 9/2008 | Vestweber et al. |
| 2009/0302742 A1 | 12/2009 | Komori et al. |
| 2011/0062429 A1 | 3/2011 | Kai et al. |
| 2012/0104943 A1 | 5/2012 | Kato et al. |

FOREIGN PATENT DOCUMENTS

| | | |
|---|---|---|
| JP | 2001-31378 A | 9/2001 |
| JP | 2003-515897 A | 5/2003 |
| JP | 2004-204234 A | 7/2004 |
| JP | 2006-135146 A | 5/2006 |
| JP | 2006-193729 A | 7/2006 |
| JP | 2008-545630 A | 12/2008 |
| JP | 2010-135467 A | 6/2010 |
| WO | WO 01/41512 | 6/2001 |
| WO | WO-2007/063754 A1 | 6/2007 |
| WO | WO-2009/136595 | 11/2009 |
| WO | WO-2009/148015 A1 | 12/2009 |
| WO | WO-2010/107244 A2 | 9/2010 |
| WO | WO-2010/126234 A1 | 11/2010 |

OTHER PUBLICATIONS

Supplementary European Search Report for the Application No. EP 12 75 7159 dated Aug. 19, 2014.
Data Base Registry [Online] Chemical Abstracts Service, Columbus, Ohio, US; Dec. 28, 1985, XP002727163, retrieved from STN Database accession No. 99573-96-3.
International Search Report for the Application No, PCT/JP2012/052937 mailed Mar. 6, 2012.
English Translation of Written Opinion of the International Searching Authority (PCT/ISA1237) for Application No. PCT/JP2012/052937 mailed Sep. 26, 2013.

*Primary Examiner* — Andrew K Bohaty
(74) *Attorney, Agent, or Firm* — Cheng Law Group, PLLC

(57) ABSTRACT

Provided are a nitrogen-containing aromatic compound useful for an organic electroluminescent device, and an organic electroluminescent device (organic EL device) that improves luminous efficiency of the device and sufficiently ensures driving stability of the device. The nitrogen-containing aromatic heterocyclic compound is represented by the following formula (1). The organic EL device includes an organic layer that contains the nitrogen-containing aromatic heterocyclic compound between an anode and a cathode laminated on a substrate. In the formula (1), a ring A represents an aromatic ring represented by the formula (1a) and fused with two adjacent rings, a ring B represents a heterocycle represented by the formula (1b) and fused with two adjacent rings, Y's each represent C—R or N, X's each represent N—Z, O, S, or Se, R represents hydrogen, an alkyl group, an aromatic group, or the like, and Z represents an alkyl group, an aromatic group, or the like.

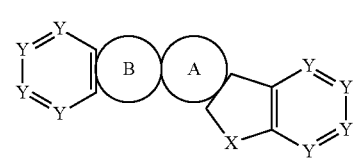

(1)

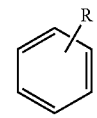

(1a)

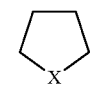

(1b)

8 Claims, 1 Drawing Sheet

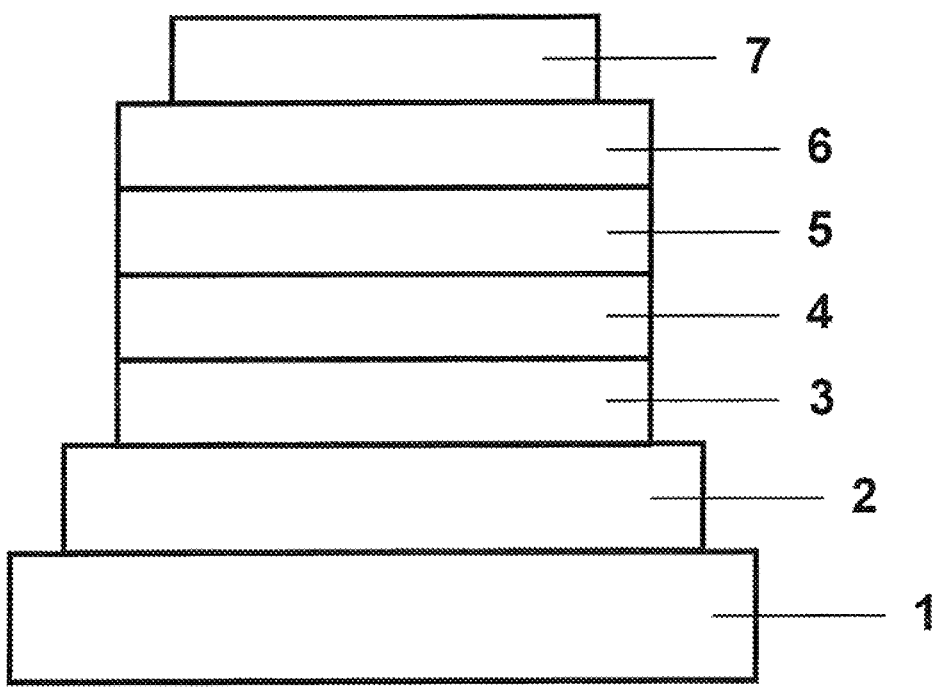

NITROGEN-CONTAINING AROMATIC COMPOUNDS AND ORGANIC ELECTROLUMINESCENT DEVICE

TECHNICAL FIELD

The present invention relates to a novel nitrogen-containing aromatic compound and an organic electroluminescent device using the compound, and more specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer there between in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are provided between electrodes as thin films, resulting in a significant improvement in luminous efficiency, compared with conventional devices in which a single crystal of anthracene or the like is used. Thus, the development of the above-mentioned organic EL device has been promoted in order to accomplish its practical application to a high-performance flat panel or organic EL lighting equipment having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies on a phosphorescent light-emitting dopant material centered on an organic metal complex such as an iridium complex have been made, as described in Patent Literature 1, for the purpose of attaining the high efficiency and long lifetime of light emission.

In order to obtain high luminous efficiency, host materials that are used with the dopant materials described above play an important role. Typical examples of the host materials proposed include 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine) iridium complex (hereinafter referred to as $Ir(ppy)_3$), a charge injection balance is disturbed because CBP has the characteristic of facilitating the delivery of holes and not facilitating the delivery of electrons. Thus, excessively delivered holes flow out into an electron-transporting layer side, with the result that the luminous efficiency from $Ir(ppy)_3$ lowers.

In order to provide high luminous efficiency to an organic EL device, it is necessary to use a host material that has high triplet excitation energy, and is striking a good balance in both charge (hole and electron)-injecting/transporting property. Further desired is a compound that has electrochemical stability, has high heat resistance, and has excellent amorphous stability, and hence further improvement has been demanded.

Patent Literature 3 discloses such an indolocarbazole compound as shown below. However, the literature merely discloses a peripherally substituted derivative useful for an organic semiconductor.

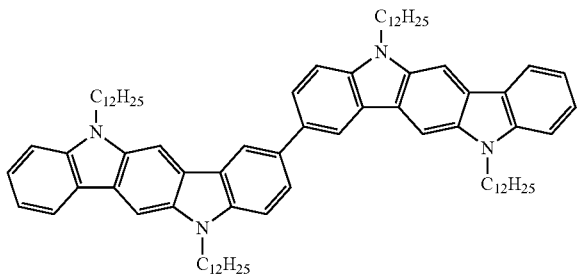

Patent Literature 4 discloses such an indolocarbazole compound as shown below. However, the literature merely discloses a copolymer with fluorene as a blue light-emitting polymer.

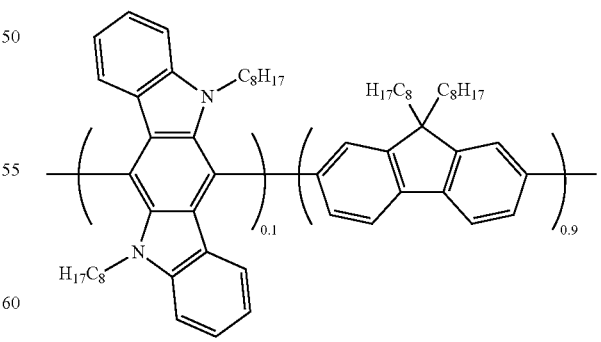

Further, Patent Literature 5 discloses such an indolo carbazole compound as shown below. However, the literature merely discloses a compound in which a plurality of indolocarbazole skeletons are linked together.

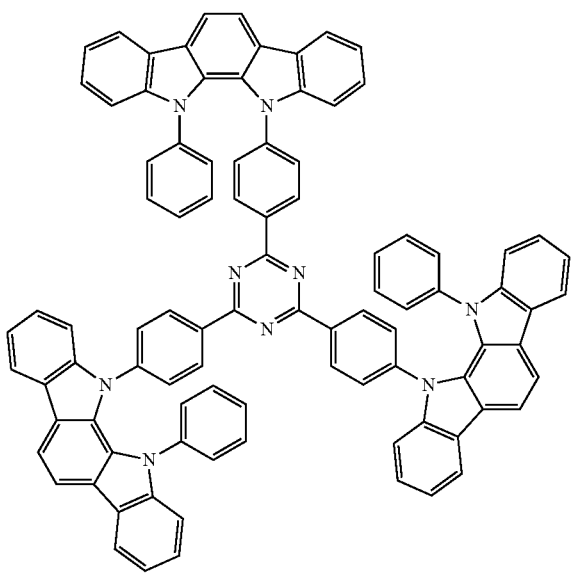 [SMILES: c1ccc(-n2c3ccccc3c3ccc4c5ccccc5n(-c5ccc(-c6nc(-c7ccc(-n8c9ccccc9c9ccc%10c%11ccccc%11n(-c%11ccccc%11)c%10c98)cc7)nc(-c7ccc(-n8c9ccccc9c9ccc%10c%11ccccc%11n(-c%11ccccc%11)c%10c98)cc7)n6)cc5)c4c32)cc1]

In addition, Patent Literatures 6 and 7 disclose an enormous range of general formulae including an indolocarbazole structure, but neither disclose nor suggest any compound in which heteroatoms are introduced into benzene rings at both terminals of an indolocarbazole.

CITATION LIST

Patent Literature

[PTL 1] JP 2003-515897 W
[PTL 2] JP 2001-313178 A
[PTL 3] JP 2006-193729 A
[PTL 4] JP 2004-204234 A
[PTL 5] WO 2007/063754 A1
[PTL 6] JP 2008-545630 W
[PTL 7] WO 2009/148015 A1

SUMMARY OF INVENTION

In order to apply an organic EL device to lighting equipment or a display device in a flat panel display or the like, it is necessary to improve the luminous efficiency of the device and also to ensure sufficiently the stability in driving the device. The present invention has an object to provide, in view of the above-mentioned circumstances, an organic EL device, which has high efficiency, has high driving stability, and is practically useful and a compound suitable for the organic EL device.

The inventors of the present invention have made extensive studies, and as a result, have found that when a nitrogen-containing aromatic compound having a specific structure shown in the next paragraph is used in an organic EL device, excellent characteristics are exhibited. Thus, the inventors have completed the present invention.

The present invention relates to a nitrogen-containing aromatic compound, which is represented by the general formula (1).

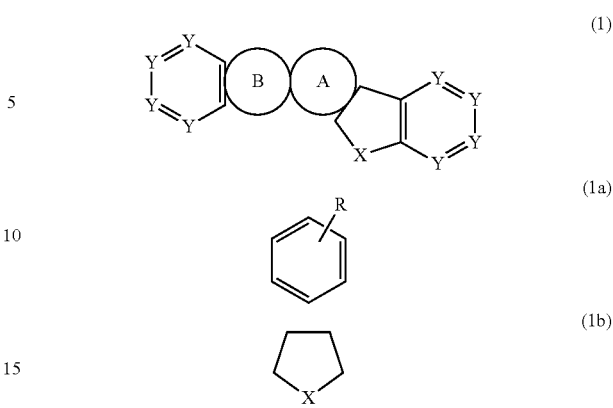

In the formula (1), a ring A represents an aromatic ring represented by the formula (1a) and fused with two adjacent rings at arbitrary positions; a ring B represents a heterocycle represented by the formula (1b) and fused with two adjacent rings at arbitrary positions; Y's each represent C—R or N, provided that one to four of Y's each represent N; X's each represent N—Z, O, S, or Se; R represents hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms and free of a fused heterocycle having four or more rings; and Z represents an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms and free of a fused heterocycle having four or more rings.

Of the nitrogen-containing aromatic compounds each represented by the general formula (1), a compound represented by the following general formula (2) is given as a preferred compound.

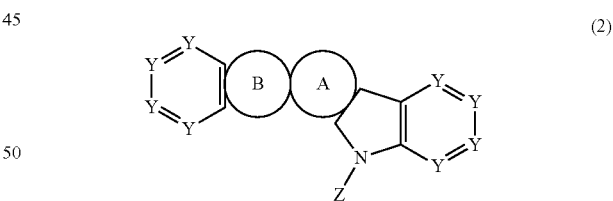

In the general formula (2), a ring A, a ring B, Y's, and Z have the same meanings as those in the general formula (1).

In the general formula (2), it is preferred that X in the ring B represent N—Z or one or two of Y's each represent N. Further, in the general formula (1), it is preferred that one or two of Y's each represent N.

The present invention also relates to an organic electroluminescent device, including the nitrogen-containing aromatic compound represented by the general formula (1) or (2).

In the organic electroluminescent device of the present invention, an organic layer that contains the compound represented by the general formula (1) or (2) preferably includes at least one layer selected from a light-emitting layer, a hole-transporting layer, an electron-transporting layer, and a hole-blocking layer. In addition, in the phosphorescent light-emitting device of the present invention, the organic layer that contains the compound represented by the general formula (1) or (2) is more preferably a light-emitting layer or a hole-transporting layer, and the light-emitting layer is also preferably a layer that contains a phosphorescent light-emitting dopant and the compound represented by the general formula (1) or (2) as a host material.

BRIEF DESCRIPTION OF DRAWINGS

FIG. 1 is a sectional view illustrating an example of the structure of an organic EL device.

DESCRIPTION OF EMBODIMENTS

A nitrogen-containing aromatic compound of the present invention is represented by the general formula (1). The nitrogen-containing aromatic compound of the present invention is hereinafter sometimes referred to as compound of the present invention or compound represented by the general formula (1).

In the general formula (1), a ring A represents an aromatic ring represented by the formula (1a) and fused with two adjacent rings at arbitrary positions. In addition, a ring B represents a heterocycle represented by the formula (1b) and fused with two adjacent rings at arbitrary positions. However, in the formula (1b), the ring cannot be fused with the adjacent rings on sides including X, and hence the kind of skeletons of the general formula (1) is limited.

In the formula (1b), X's each independently represent N—Z, O, S, or Se, preferably N—Z, O, or S, more preferably N—Z.

In this case, Z represents an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms and free of a fused heterocycle having four or more rings. It is preferred that Z represent an alkyl group having 1 to 20 carbon atoms, a cycloalkyl group having 3 to 20 carbon atoms, an alkenyl group having 2 to 20 carbon atoms, an alkynyl group having 2 to 20 carbon atoms, an aromatic hydrocarbon group having 6 to 30 carbon atoms, or an aromatic heterocyclic group having 3 to 30 carbon atoms and free of a fused heterocycle having four or more rings. When X's each represent N—Z, two Z's are present in the general formula (1), and the two Z's may be identical to or different from each other. Herein, the aromatic heterocyclic group is free of a fused heterocycle having four or more rings. In addition, any such group is free of a fused heterocycle having four or more rings as a substituent.

When Z represents an alkyl group having 1 to 30 carbon atoms, the number of carbon atoms of the group is preferably 1 to 20, more preferably 1 to 10. Specific examples of the alkyl group in the case of having no substitution include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. The alkyl group may be linear or branched.

The alkyl group may have a substituent, and when the group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When the alkyl group has a substituent, the total number of substituents is 1 to 10. The number is preferably 1 to 6, more preferably 1 to 4. In addition, when the group has two or more substituents, the substituents may be identical to or different from each other.

Herein, in the calculation of the number of carbon atoms, when the group has a substituent, the number of carbon atoms of the substituent is also included.

When Z represents a cycloalkyl group having 3 to 30 carbon atoms, the number of carbon atoms of the group is preferably 3 to 20, more preferably 5 to 10. Specific examples of the cycloalkyl group in the case of having no substitution include a cyclopropyl group, a cyclobutyl group, a cyclopentyl group, a cyclohexyl group, a cycloheptyl group, a cyclooctyl group, cyclohexyl group, and decahydronaphthyl group. Preferred examples thereof include a cyclopentyl group and a cyclohexyl group.

The cycloalkyl group may have a substituent, and when the group has a substituent, the substituent is an alkyl group having 1 to 10 carbon atoms, an aromatic hydrocarbon group having 6 to 18 carbon atoms, or an aromatic heterocyclic group having 3 to 18 carbon atoms.

When the cycloalkyl group has a substituent, the total number of substituents is 1 to 10. The number is preferably 1 to 6, more preferably 1 to 4. In addition, when the group has two or more substituents, the substituents may be identical to or different from each other.

When Z represents an alkenyl group having 2 to 30 carbon atoms or an alkynyl group having 2 to 30 carbon atoms, the number of carbon atoms of the group is preferably 2 to 20, more preferably 2 to 10. Specific examples of the alkenyl group and the alkynyl group in the case of having no substitution include an ethylenyl group, a propylenyl group, a butenyl group, a pentenyl group, a hexenyl group, a heptenyl group, an octenyl group, an acetylenyl group, a propynyl group, a butynyl group, and a pentynyl group. Preferred examples thereof include an ethylenyl group, a propylenyl group, a butenyl group, an acetylenyl group, and a propynyl group. The alkenyl group and the alkynyl group may be linear or branched.

The alkenyl group or the alkynyl group may have a substituent, and when any such group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When Z represents an aromatic hydrocarbon group having 6 to 50 carbon atoms, the number of carbon atoms of the group is preferably 6 to 30, more preferably 6 to 18. When Z represents an aromatic heterocyclic group having 3 to 50 carbon atoms, the number of carbon atoms of the group is preferably 3 to 30, more preferably 3 to 18. In this case, the aromatic heterocyclic group is free of a fused heterocycle having four or more rings.

Specific examples of the aromatic hydrocarbon group and the aromatic heterocyclic group in the case of having no substitution include a monovalent group produced by removing hydrogen from benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphtene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, or an aromatic compound in which a plurality of such aromatic rings are linked together. Preferred examples thereof include a monovalent group produced by removing hydrogen from benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, or an aromatic compound in which a plurality of such aromatic rings are linked together.

It should be noted that in the case of the group produced from an aromatic compound in which a plurality of aromatic rings are linked together, the number of the aromatic rings to be linked together is preferably 2 to 10, more preferably 2 to 7, and the aromatic rings to be linked together may be identical to or different from each other. In that case, the bonding position of A to be bonded to nitrogen is not limited, and A may be bonded to a ring at a terminal portion of linked aromatic rings or may be bonded to a ring at the central portion thereof. Herein, the term "aromatic ring" is a generic term for an aromatic hydrocarbon ring and an aromatic heterocycle. In addition, when the linked aromatic rings include at least one heterocycle, the linked aromatic rings are included in the category of the aromatic heterocyclic group.

Herein, the monovalent group produced by the linking of a plurality of aromatic rings is, for example, represented by any one of the following formulae.

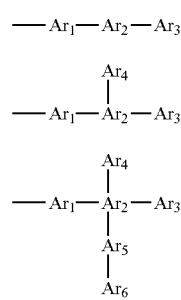

(In the formulae (3) to (5), $Ar_1$ to $Ar_6$ each represent a substituted or non-substituted aromatic ring.)

Herein, the term "aromatic heterocyclic group free of a fused heterocycle having four or more rings" means a monocyclic aromatic heterocyclic group, or a fused aromatic heterocyclic group having two or three rings, and the aromatic heterocyclic group may have a substituent. It should be noted that when the aromatic heterocyclic group is, for example, such a group produced by the linking of a plurality of aromatic rings as represented by the formula (3), none of the aromatic rings is a fused aromatic heterocyclic group having four or more rings.

The aromatic hydrocarbon group or the aromatic heterocyclic group may have a substituent, and when any such group has a substituent, the substituent is an alkyl group having 1 to 20 carbon atoms, a cycloalkyl group having 3 to 20 carbon atoms, an alkoxy group having 1 to 20 carbon atoms, an acyl group having 2 to 20 carbon atoms, a dialkylamino group having 2 to 20 carbon atoms, a diarylamino group having 6 to 28 carbon atoms, a phosphanyl group having 6 to 18 carbon atoms, or a silyl group having 3 to 18 carbon atoms. The substituent is preferably an alkyl group having 1 to 4 carbon atoms, a cycloalkyl group having 3 to 6 carbon atoms, or a diarylamino group having 6 to 20 carbon atoms. It should be noted that, when a plurality of aromatic rings are linked together in the aromatic hydrocarbon group or the aromatic heterocyclic group, an aromatic group to be linked in a branched fashion is not treated as the substituent. In addition, when the substituent is any one of a dialkylamino group and a diarylamino group, two alkyl groups and aryl groups may be identical to or different from each other, and the aryl groups may be heterocyclic groups.

When Z represents an aromatic hydrocarbon group or an aromatic heterocyclic group, and the group has a substituent, the total number of substituents is 1 to 10. The number is preferably 1 to 6, more preferably 1 to 4. In addition, when the group has two or more substituents, the substituents may be identical to or different from each other.

In the general formula (1), R's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 30 carbon atoms, or an aromatic heterocyclic group having 3 to 30 carbon atoms and free of a fused heterocycle having four or more rings. R's each preferably represent hydrogen, an alkyl group having 1 to 20 carbon atoms, a cycloalkyl group having 3 to 20 carbon atoms, an alkenyl group having 2 to 20 carbon atoms, an alkynyl group having 2 to 20 carbon atoms, an aromatic hydrocarbon group having 6 to 20 carbon atoms, or an aromatic heterocyclic group having 3 to 20 carbon atoms and free of a fused heterocycle having four or more rings.

Specific examples of the alkyl group, the cycloalkyl group, the alkenyl group, or the alkynyl group are identical to those of the alkyl group, cycloalkyl group, alkenyl group, or alkynyl group constituting Z. In addition, description in the case of Z holds true for the case where such alkyl group, cycloalkyl group, alkenyl group, or alkynyl group has a substituent.

Specific examples of the aromatic hydrocarbon group or the aromatic heterocyclic group free of a fused heterocycle having four or more rings are identical to those of the aromatic hydrocarbon group or aromatic heterocyclic group free of a fused heterocycle having four or more rings constituting Z except for a difference in total number of carbon atoms. In addition, the description in the case of Z holds true for the case where such aromatic hydrocarbon group or aromatic heterocyclic group has a substituent free of a fused heterocycle having four or more rings.

In the general formula (1), Y's each represent C—R or N, provided that one to four of Y's each represent N. In addition, four Y's are present in each of six-membered rings at both terminals, and the number of Y's that each represent N is preferably 2 or less in each of the rings, more preferably 2 or less in the total of the rings. It should be noted that R has the same meanings as those described above with regard to specific examples thereof.

A compound of the general formula (2) is given as a preferred aspect of the compound of the general formula (1). Common symbols have the same meanings as those in the general formula (1) except that X is specified as N—Z.

The nitrogen-containing aromatic compound of the present invention can be synthesized from an azaindole derivative as a starting material by employing a known approach after selecting raw materials in accordance with the structure of the target compound.

For example, a skeleton in the general formula (1) in which X represents N—Z can be synthesized by the following reaction formula with reference to a synthesis example described in Tetrahedron, 1999, 2371-2380.

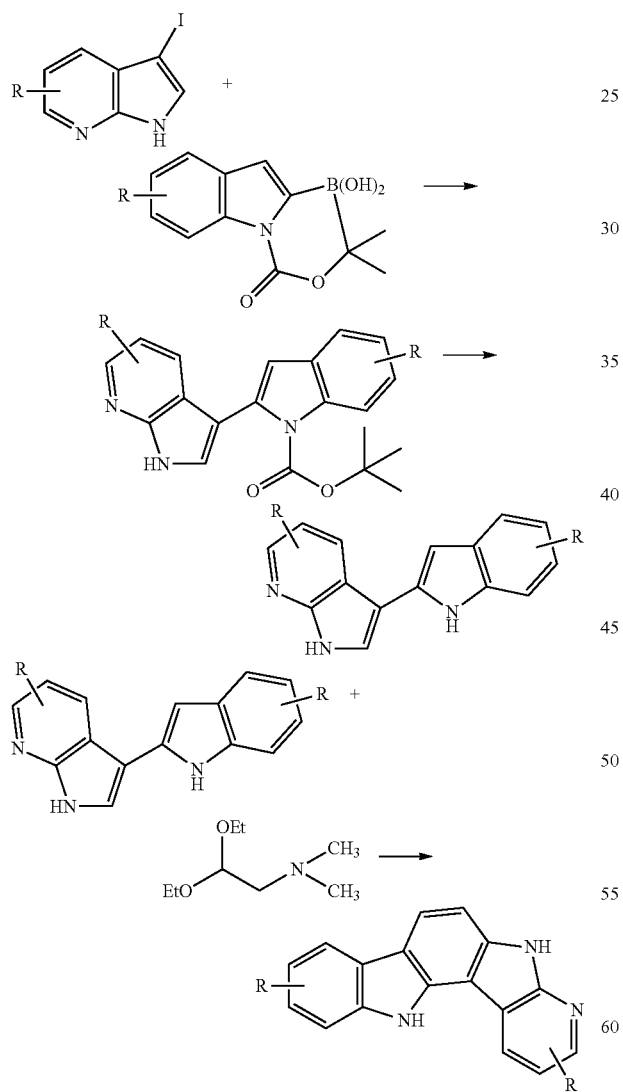

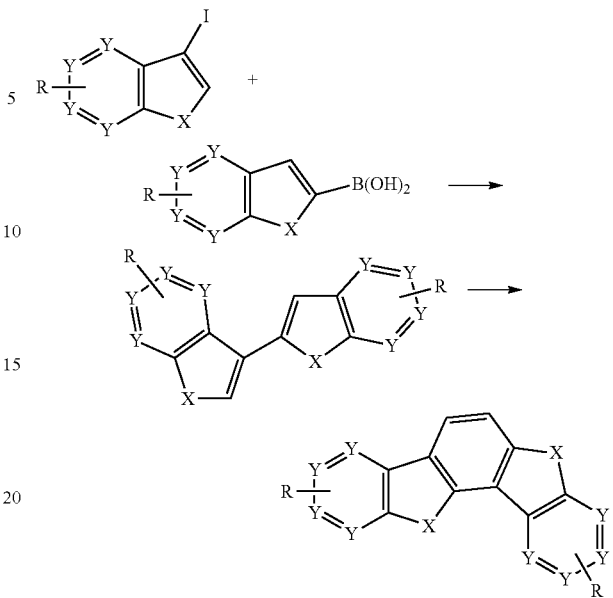

When the compound obtained according to the above-mentioned reaction formula has a nitrogen-containing five-membered heterocycle, the nitrogen-containing aromatic compound represented by the general formula (1) can be synthesized by substituting hydrogen on nitrogen in the five-membered heterocycle by the corresponding substituent through a coupling reaction such as the Ullmann reaction.

Specific examples of the compound of the present invention represented by the general formula (1) are shown below. However, the compound of the present invention is not limited thereto.

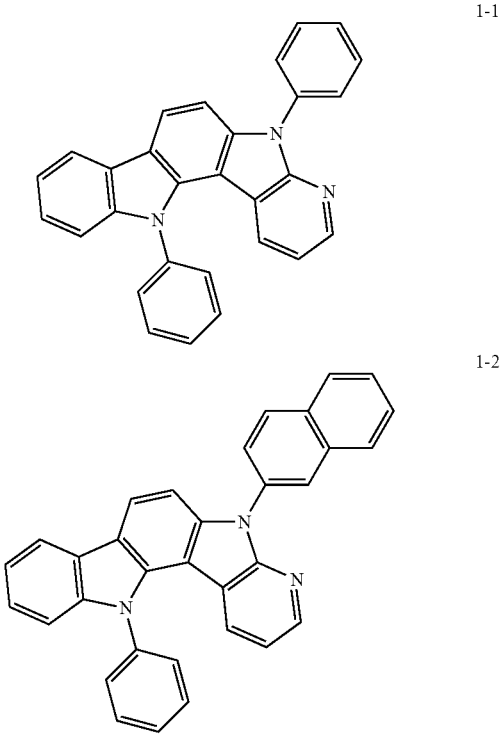

In addition, a skeleton in the general formula (1) in which X represents any one of O, S, and Se can also be synthesized by using the synthesis example.

-continued
1-3
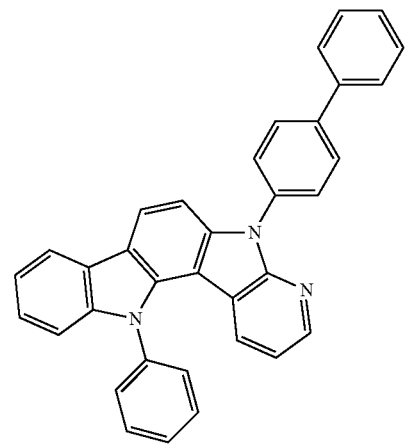
1-4
1-5
1-6
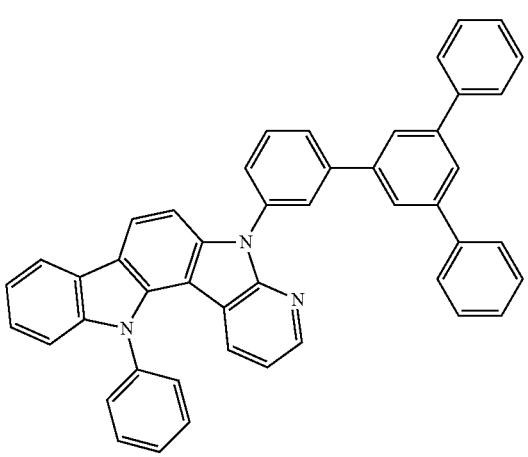
1-7
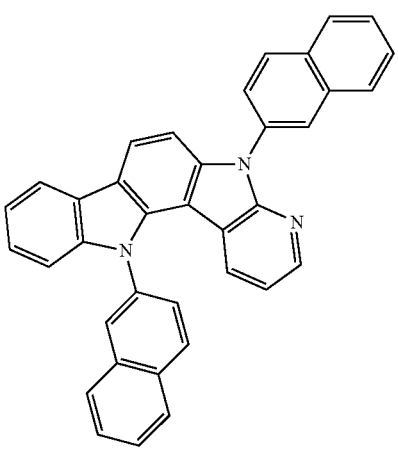
1-8
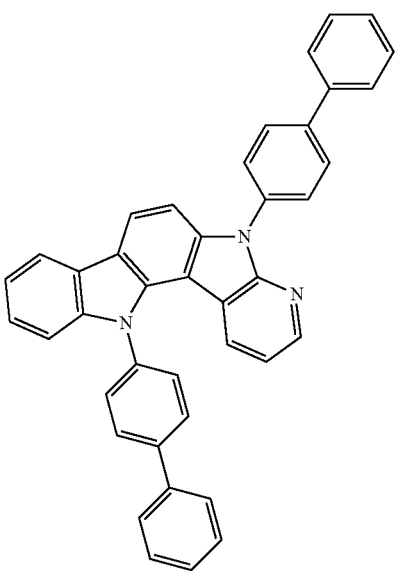

1-9
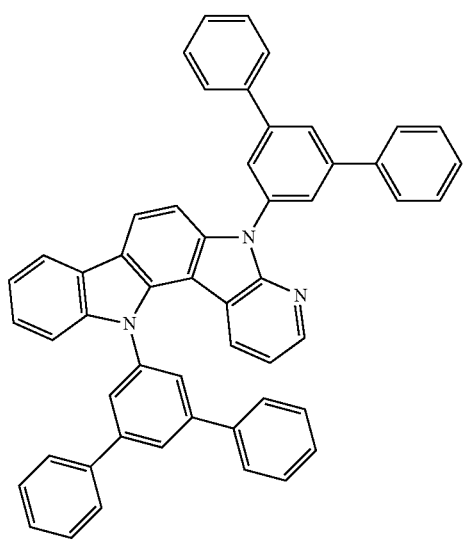
1-10
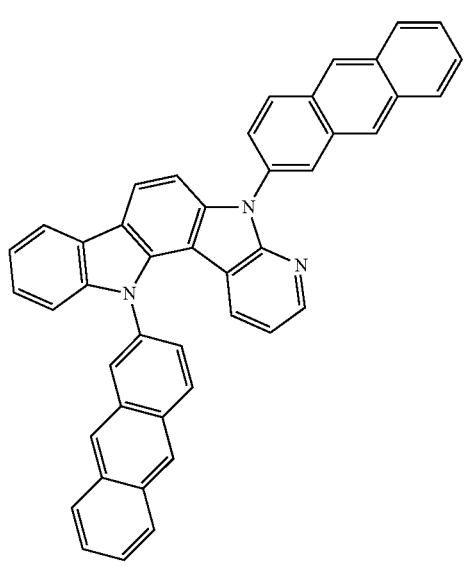
1-11
1-12
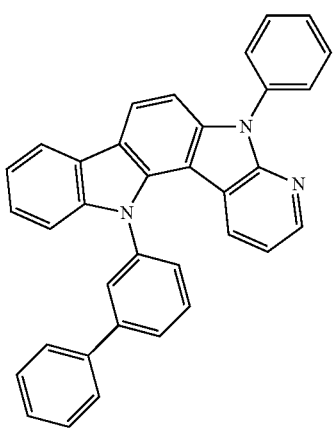
1-13
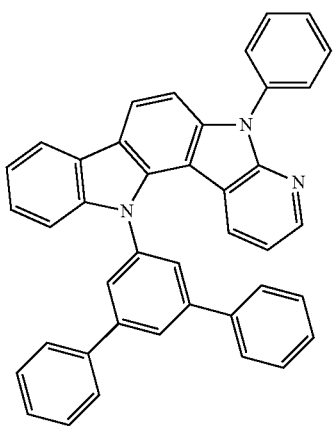
1-14
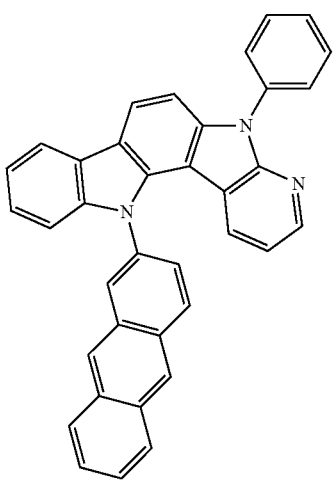

-continued
1-15
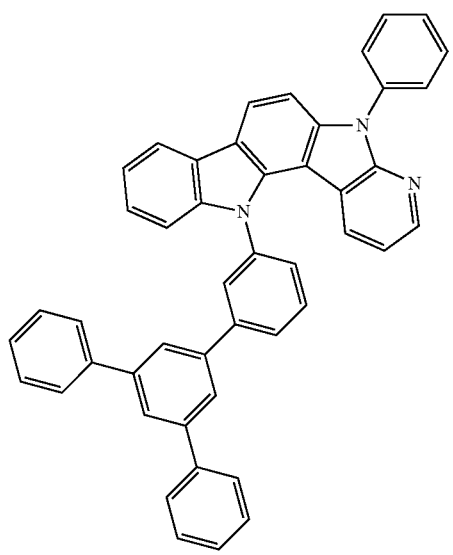
1-15
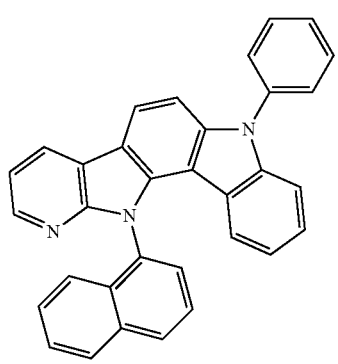
1-16
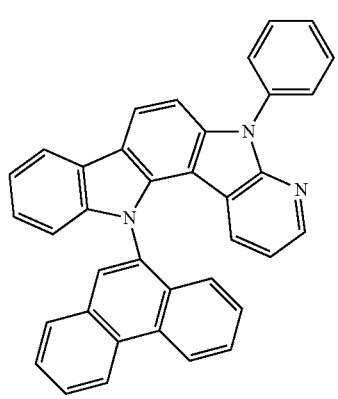
1-17
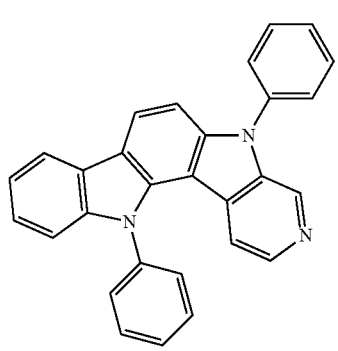
1-18
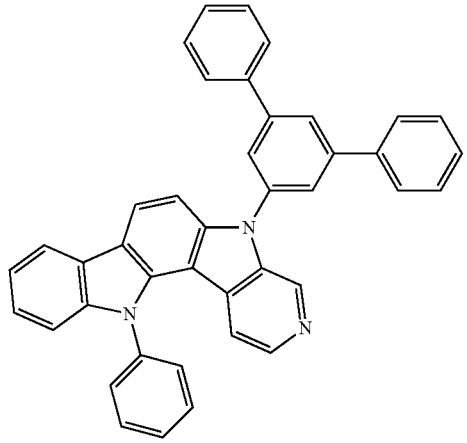
1-19
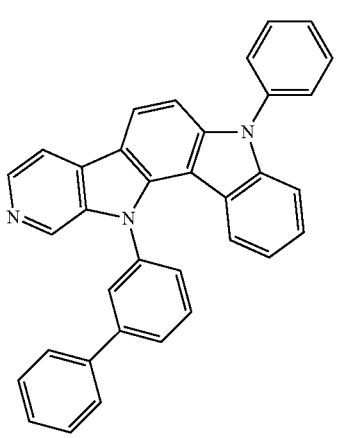
1-20
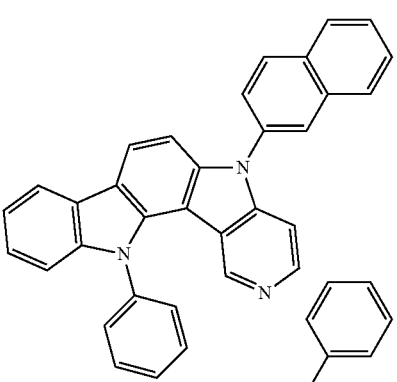
1-21
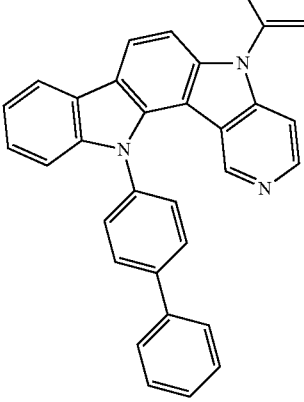

1-21
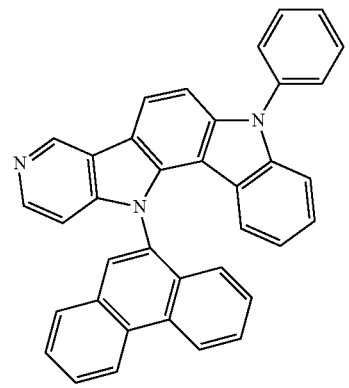
1-23
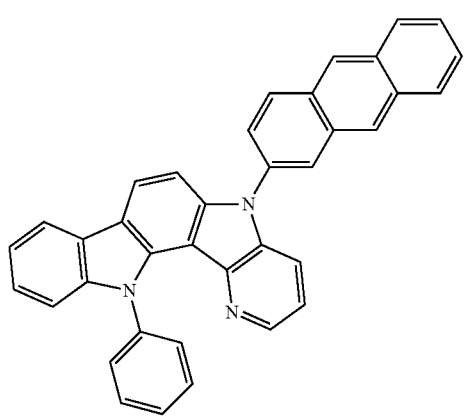
1-24
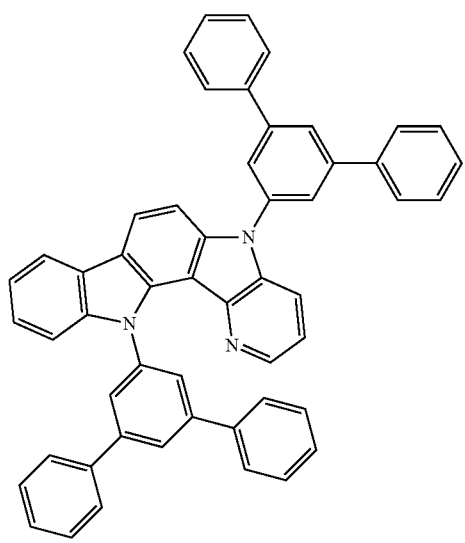
1-25
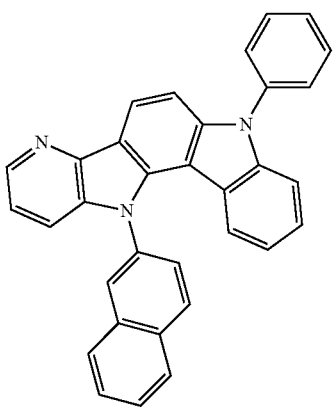
1-26
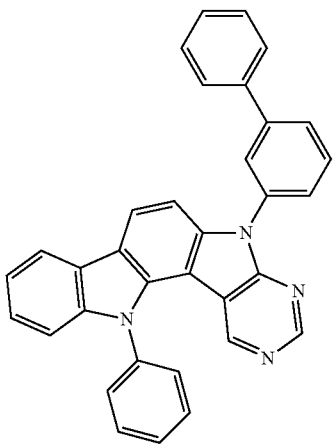
1-27
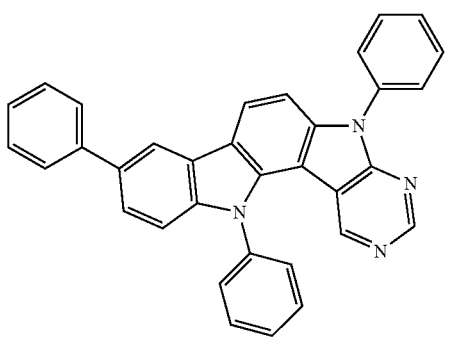
1-28
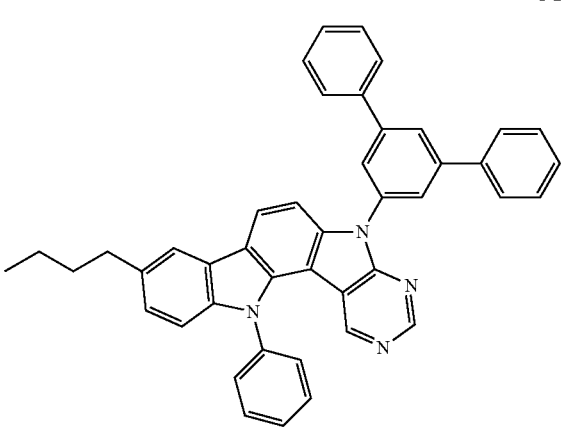

1-29
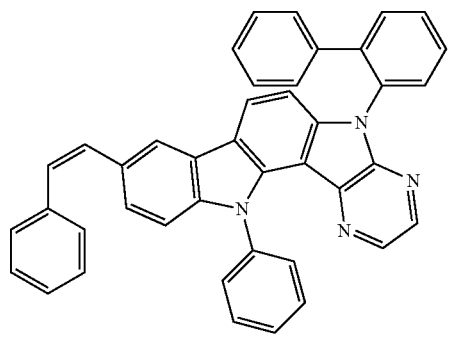
1-30
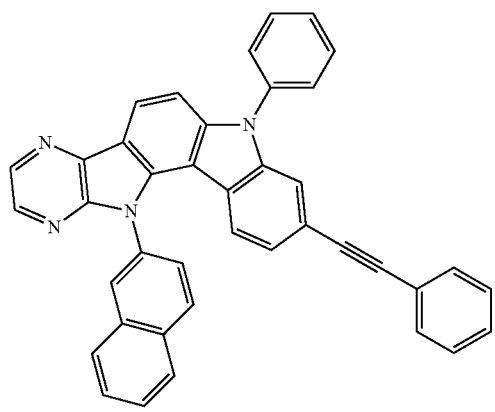
1-31
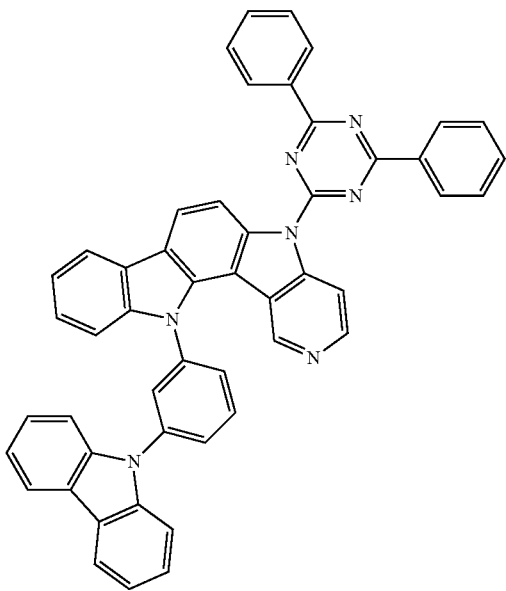
1-32
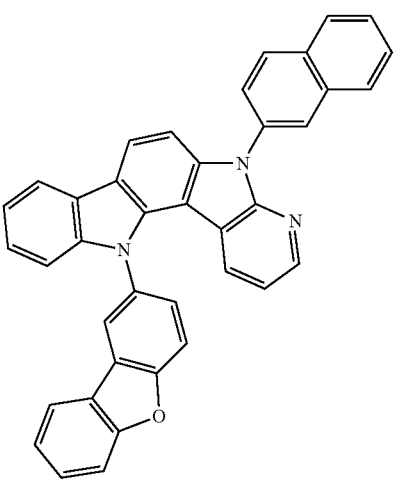
1-33
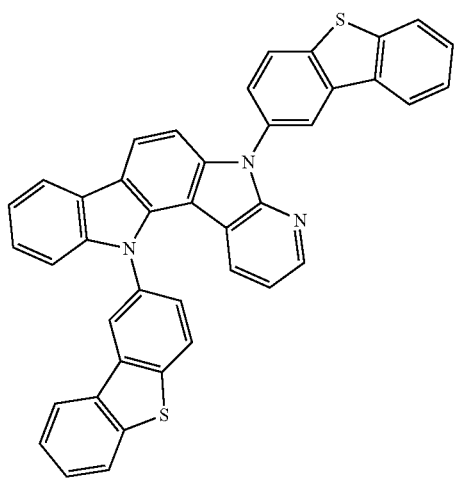
1-34
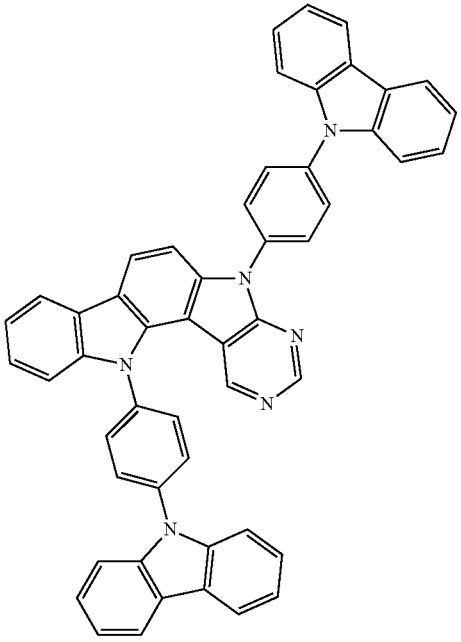

-continued
1-35
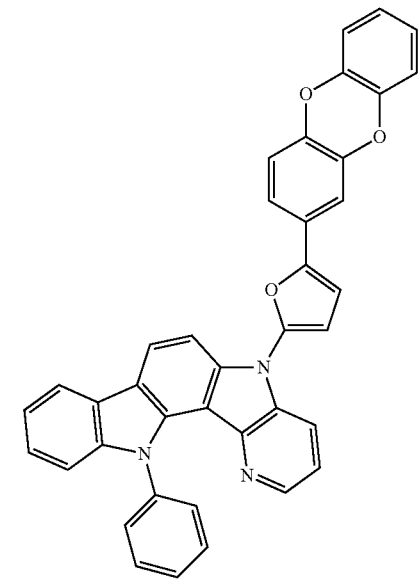
1-36
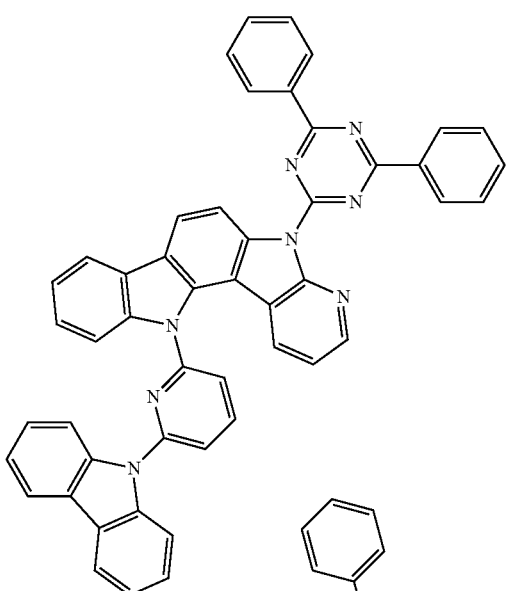
1-37
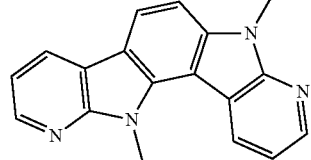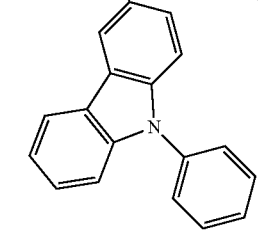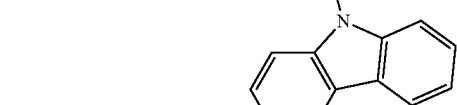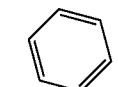
1-38
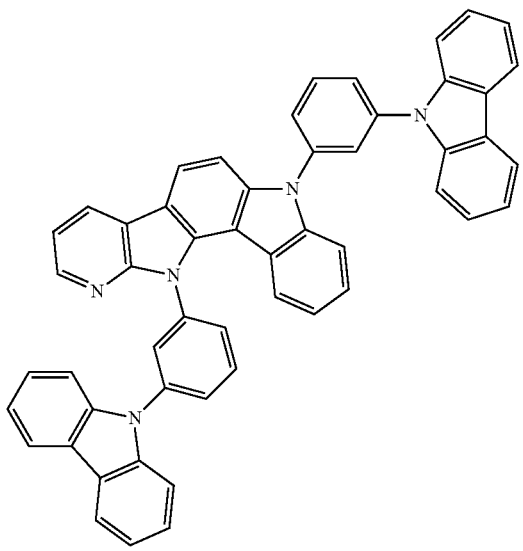
1-39
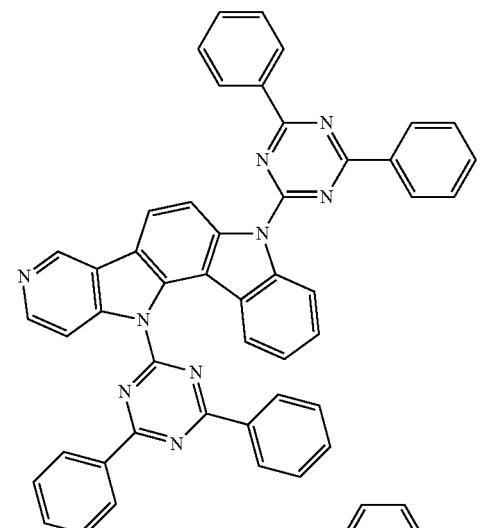
1-40
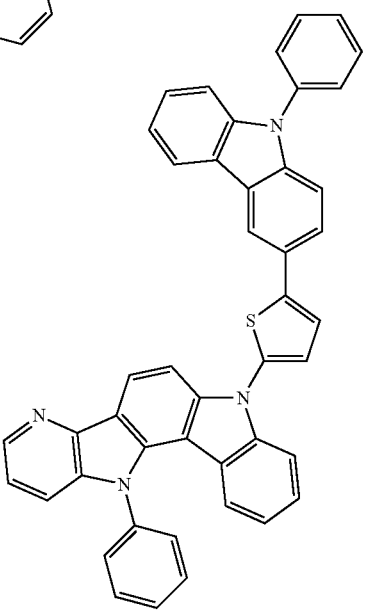

23
-continued
1-41
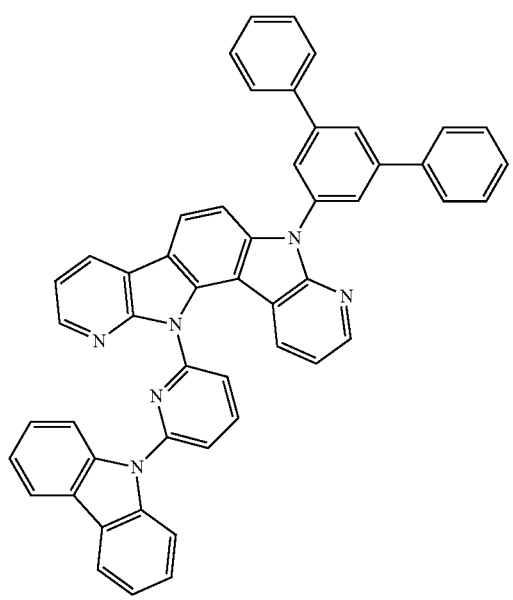
1-42
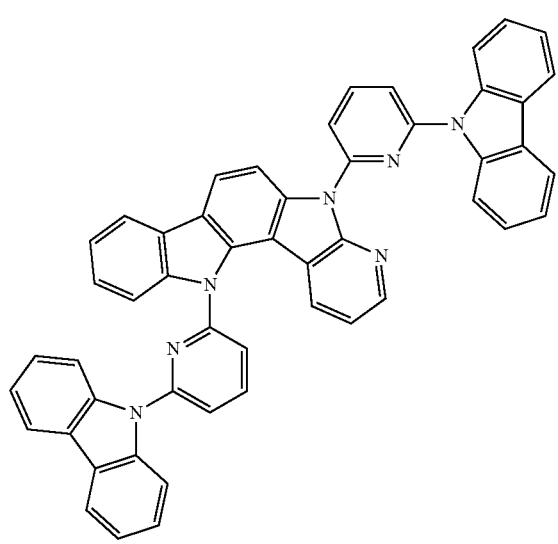
1-43
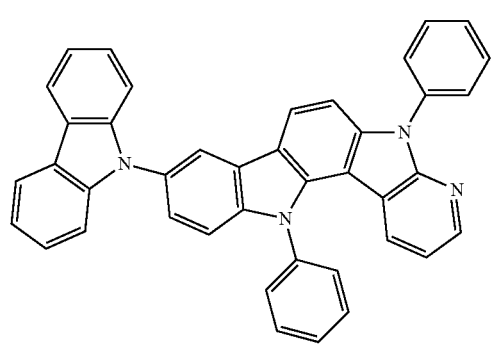
24
-continued
1-44
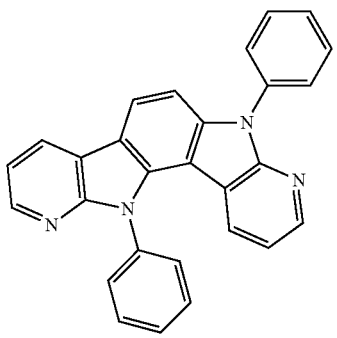
1-45
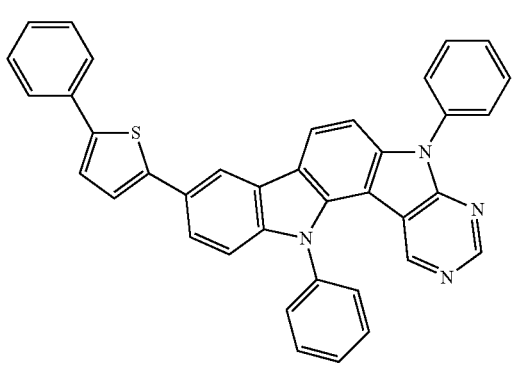
1-46
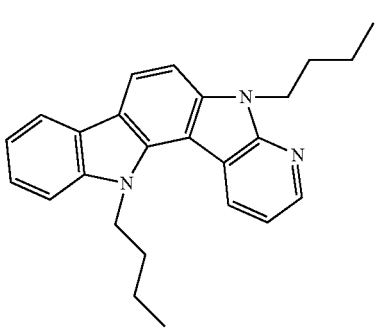
1-47
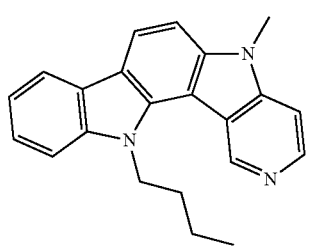
1-48
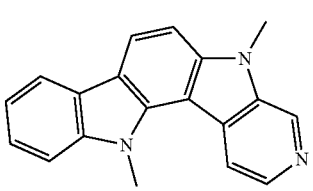

-continued
1-49
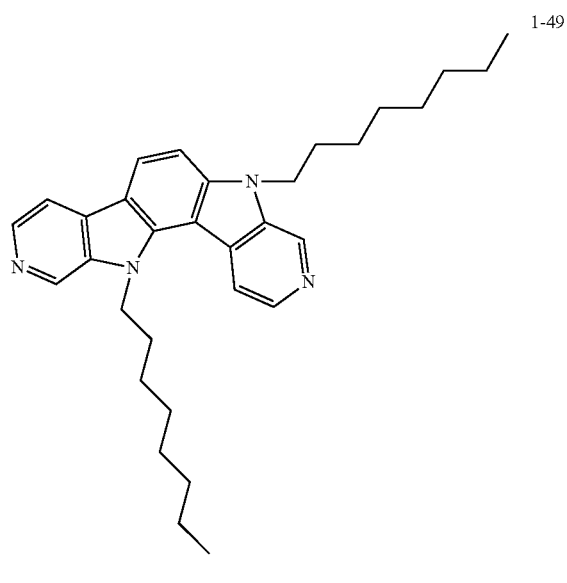
1-52
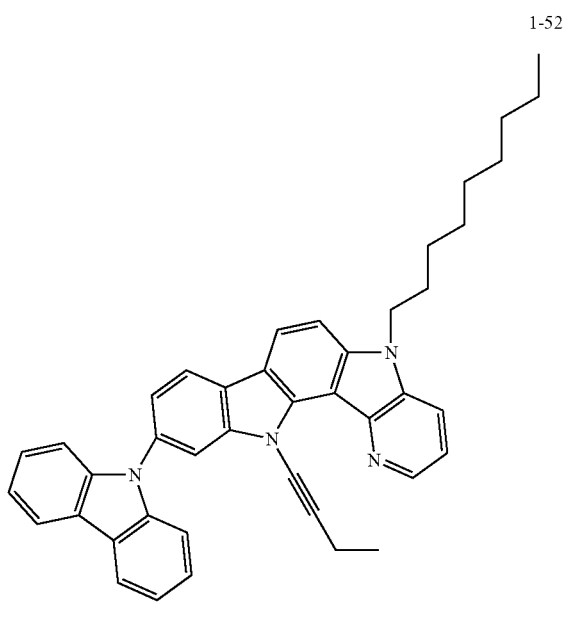
1-50
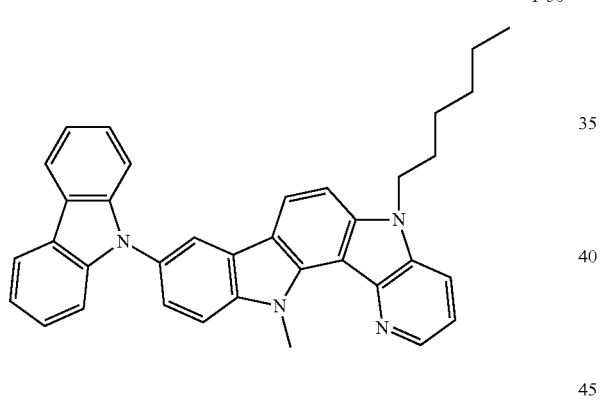
1-51
1-53
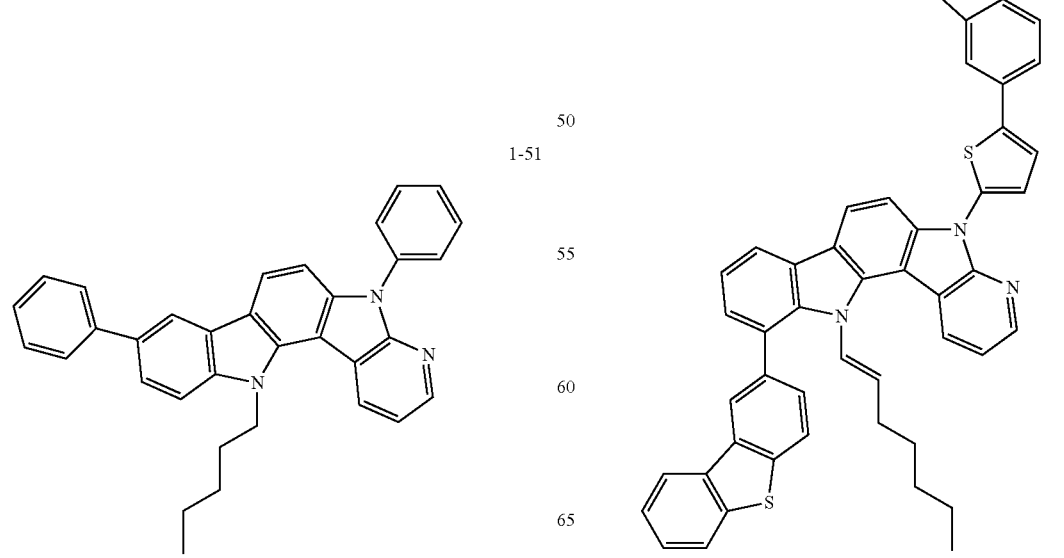

1-54
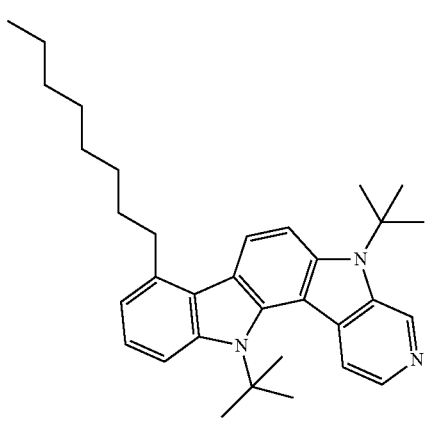
1-55
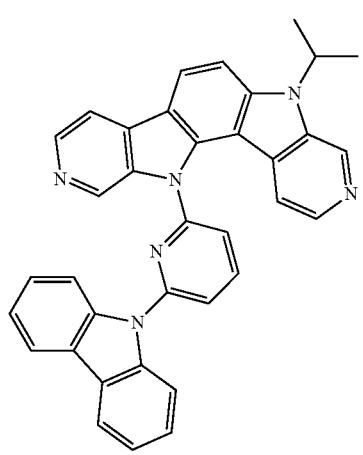
1-56
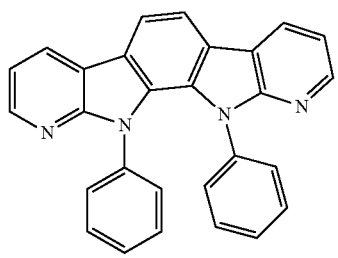
1-57
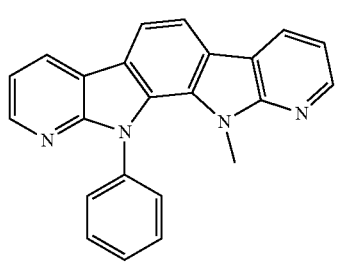
1-58
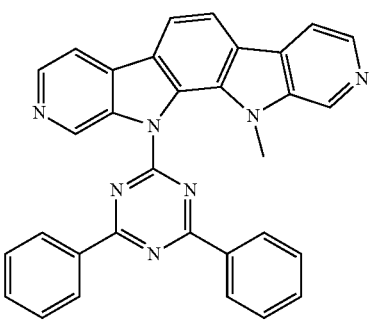
1-59
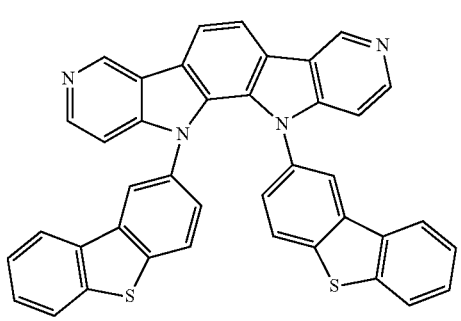
1-60
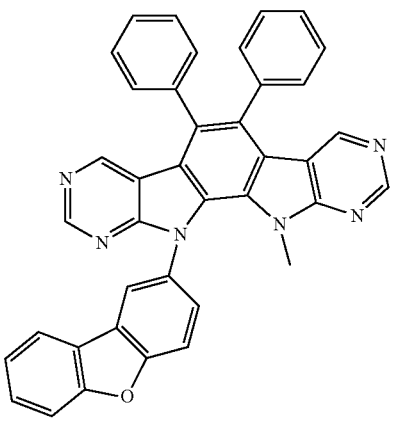
1-61
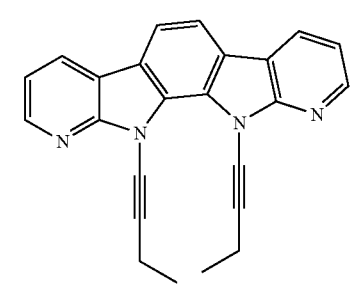

-continued
1-62
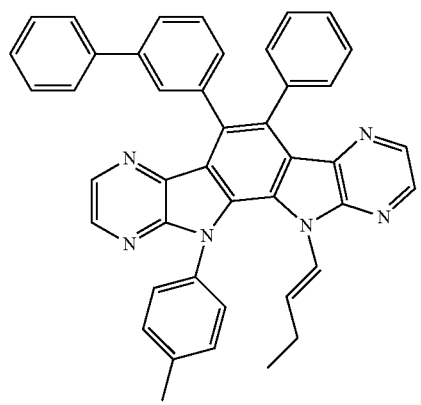
1-63
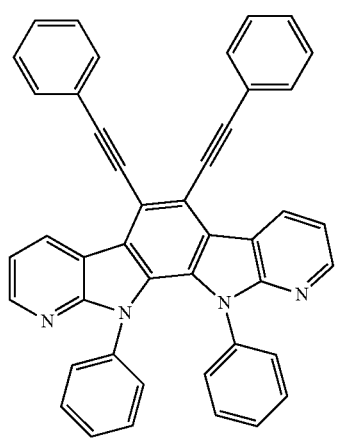
1-64
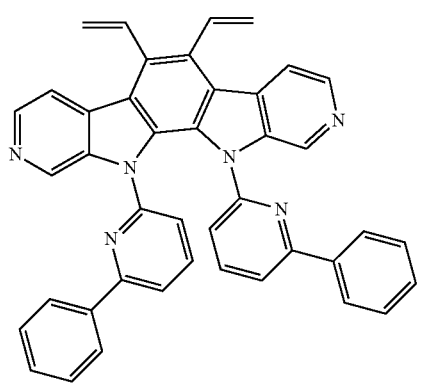
1-65
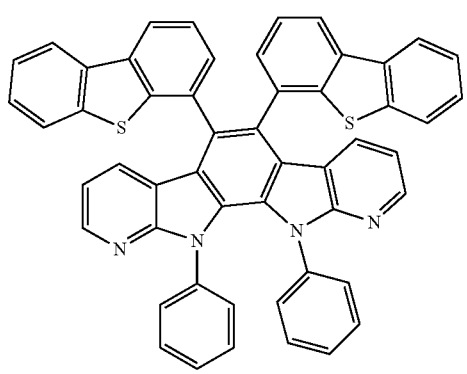
-continued
1-66
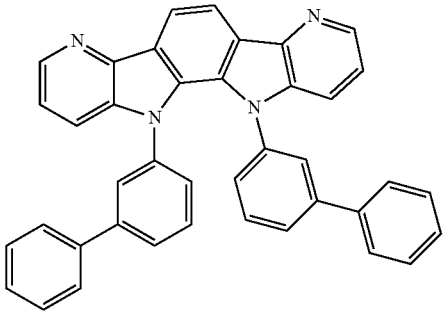
1-67
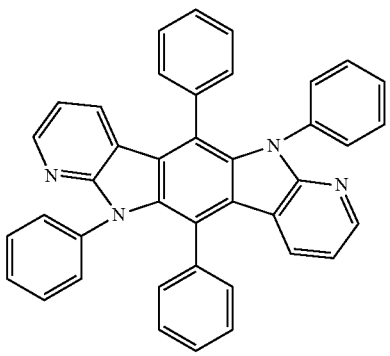
1-68
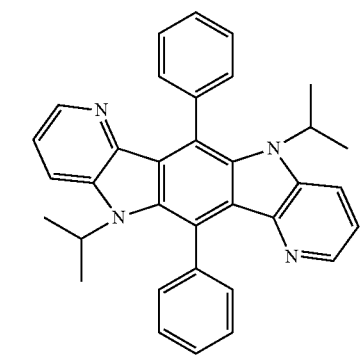
1-69
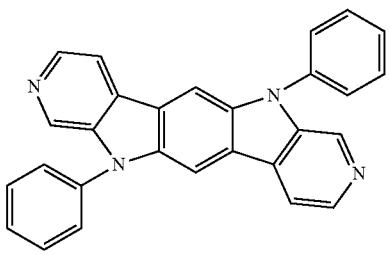

-continued
1-70
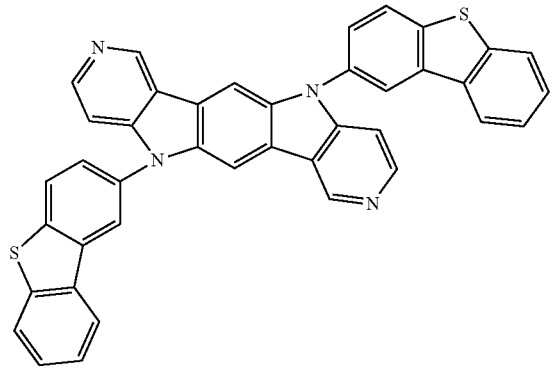
1-71
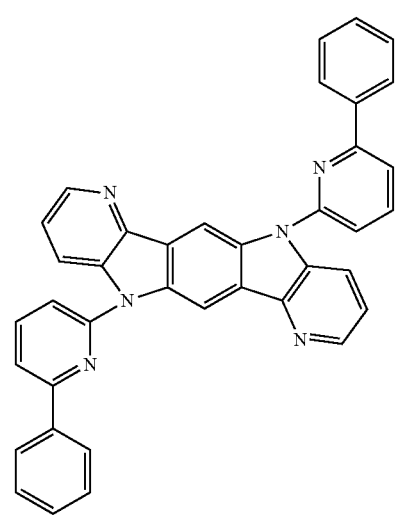
2-1
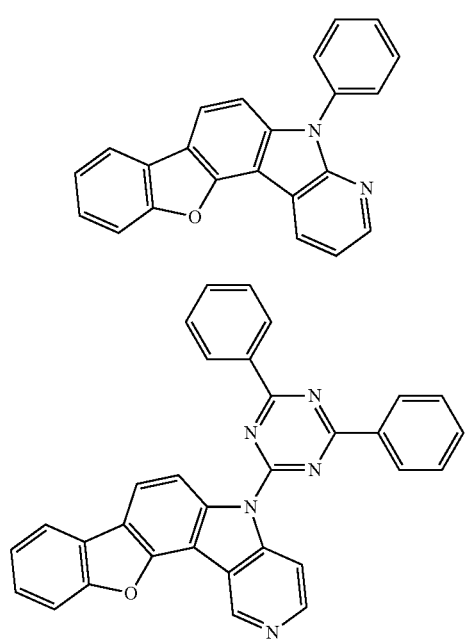
2-2
-continued
2-3
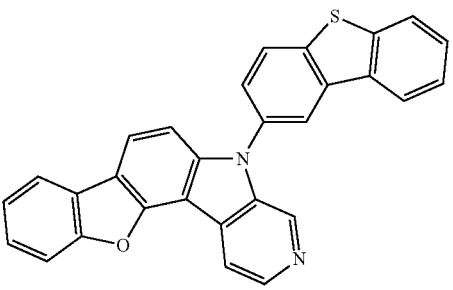
2-4
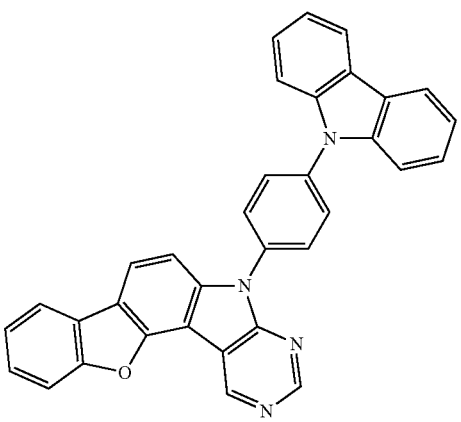
2-5
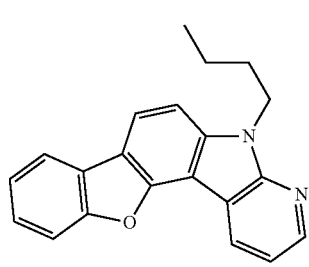
2-6
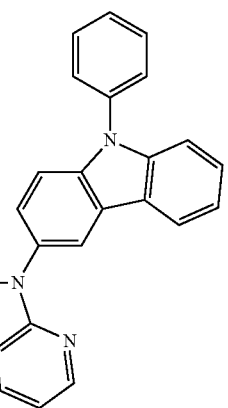

-continued
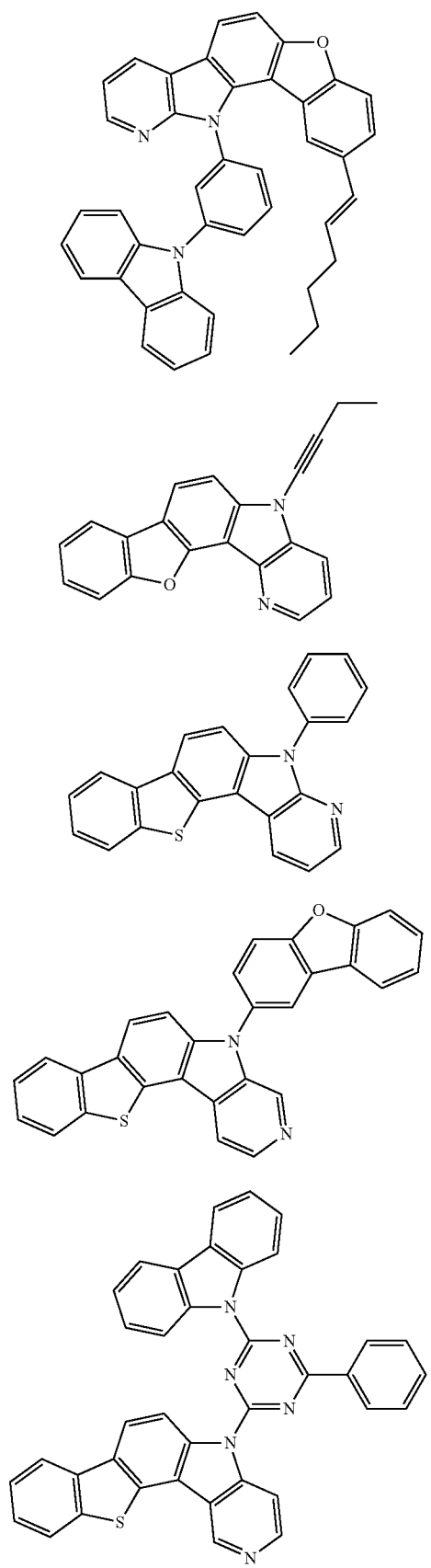
2-7
2-8
3-1
3-2
3-3
-continued
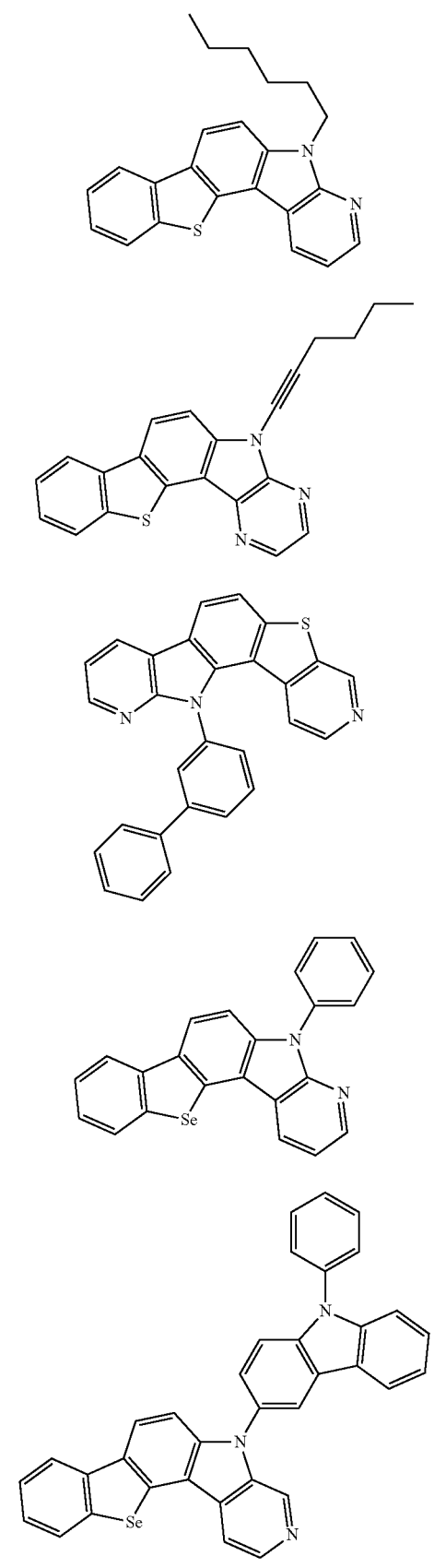
3-4
3-5
3-6
4-1
4-2

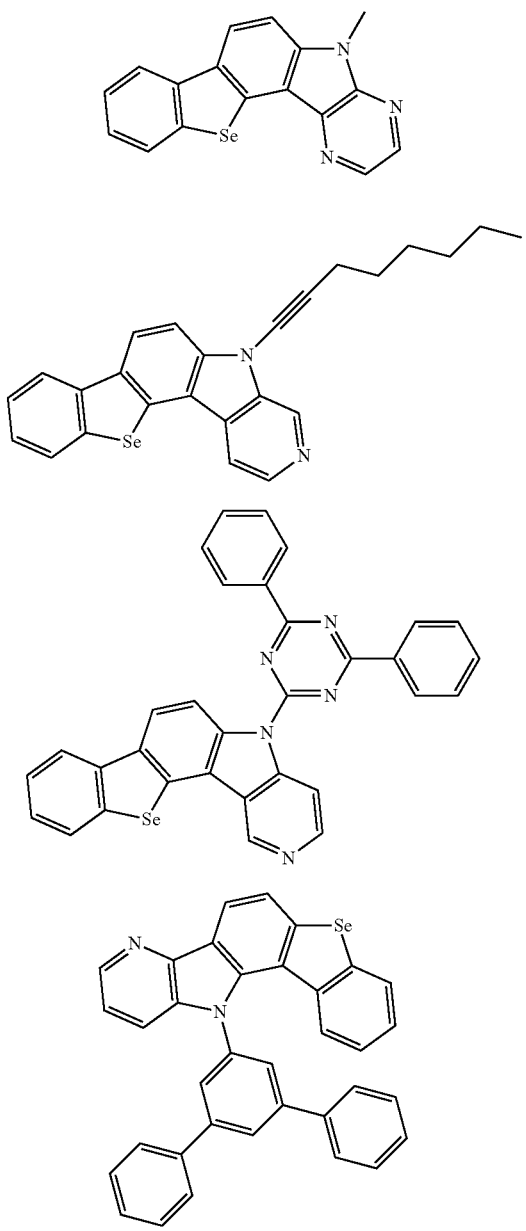

Next, an organic EL device of the present invention is described.

The organic EL device of the present invention includes at least one organic layer including a light-emitting layer between an anode and a cathode laminated on a substrate, and the at least one organic layer contains the compound represented by the general formula (1). The layer that contains the compound represented by the general formula (1) is preferably a light-emitting layer, a hole-transporting layer, an electron-transporting layer, or a hole-blocking layer, more preferably a light-emitting layer or a hole-transporting layer.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred ohms per square (Ω/□) or less.

Further, the thickness of the film is, depending on its material, selected from usually the range of 10 to 1,000 nm, preferably the range of 10 to 200 nm.

—Cathode—

On the other hand, used as the cathode is a cathode formed by using, as an electrode substance, any of a metal (referred to as "electron-injecting metal"), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by a method such as vapor deposition or sputtering. Further, the sheet resistance as the cathode is preferably several hundred $\Omega/\square$ or less, and the thickness of the film is selected from usually the range of 10 nm to 5 μm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer, which may be any one of a fluorescent light-emitting layer and a phosphorescent light-emitting layer, is preferably the phosphorescent light-emitting layer.

When the light-emitting layer is the fluorescent light-emitting layer, at least one kind of fluorescent light-emitting material may be used alone as a fluorescent light-emitting material, but it is preferred that the fluorescent light-emitting material be used as a fluorescent light-emitting dopant and a host material be incorporated.

Although the compound represented by the general formula (1) can be used as the fluorescent light-emitting material in the light-emitting layer, when the compound is used in any other organic layer, a material selected from fluorescent light-emitting materials known to the public by many patent literatures and the like can be used. Examples thereof include: a benzoxazole derivative, a benzimidazole derivative, a benzothiazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrralidine derivative, a cyclopentadiene derivative, a bisstyrylanthracene derivative, a quinacridone derivative, a pyrrolopyridine derivative, a thiadiazolopyridine derivative, a cyclopentadiene derivative, a styrylamine derivative, a diketopyrrolopyrrole derivative, and an aromatic dimethylidyne compound; various metal complexes typified by a metal complex of an 8-quinolinol derivative and a metal complex, rare earth metal complex, or transition metal complex of a pyrromethene derivative; polymer compounds such as polythiophene, polyphenylene, and polyphenylene vinylene; and an organic silane derivative. Preferred examples thereof include a fused aromatic compound, a styryl compound, a diketopyrrolopyrrole compound, an oxazine compound, and a metal complex, transition metal complex, or lanthanoid complex of pyrromethene. More preferred examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthophenanthridine, phenanthroxazole, quinolino[6,5-f]quinoline, and benzothiophanthrene. Each of those materials may have an aryl group, a heteroaromatic ring group, a diarylamino group, or an alkyl group as a substituent.

When the fluorescent light-emitting material is used as the fluorescent light-emitting dopant and the host material is incorporated, the amount of the fluorescent light-emitting dopant to be incorporated into the light-emitting layer desirably falls within the range of 0.01 to 20 wt %, preferably 0.1 to 10 wt %.

In ordinary cases, the organic EL device is caused to emit light by producing a light-emitting substance in an excited state through the injection of charge into a light-emitting substance from each of both electrodes, i.e., the anode and the cathode. It is said that in the case of a charge injection-type organic EL device, 25% of produced excitons are excited to excited singlet states and the remaining 75% are excited to excited triplet states. As described in the meeting proceedings (19p-ZK-4 and 19p-ZK-5) of the 57th Meeting of The Japan Society of Applied Physics and Related Societies, a specific fluorescent light-emitting substance is known to express thermally activated delayed fluorescence via the following mechanism. After the transition of its energy into an excited triplet state through intersystem crossing or the like, the substance undergoes inverse intersystem crossing into an excited singlet state by virtue of triplet-triplet annihilation or the absorption of a thermal energy, thereby radiating fluorescence. The organic EL device using the compound of the present invention can also express delayed fluorescence. In this case, the fluorescence can include both fluorescent emission and delayed fluorescent emission, provided that light emission from the host material may constitute part of the light emission.

In the case where the light-emitting layer is a phosphorescent light-emitting layer, a phosphorescent light-emitting dopant and a host material are incorporated. It is recommended to use, as a material for the phosphorescent light-emitting dopant, a material containing an organometallic complex including at least one metal selected from ruthenium, rhodium, palladium, silver, rhenium, osmium, iridium, platinum, and gold. Such organometallic complexes are known in the prior art documents and the like, and a complex is selected therefrom and may be used.

Preferred examples of the phosphorescent light-emitting dopant include complexes such as $Ir(ppy)_3$, complexes such as $(Bt)_2Iracac$, and complexes such as $(Btp)Ptacac$, the complexes each having a noble metal element such as Ir as a central metal. Specific examples of those complexes are shown below, but the complexes are not limited to the compounds described below.
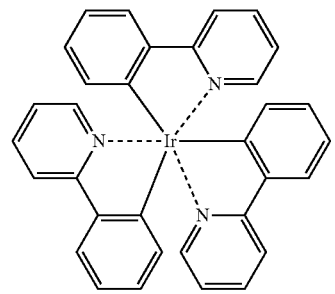
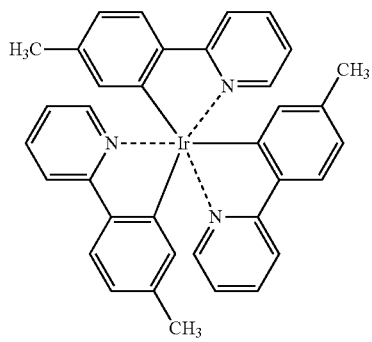
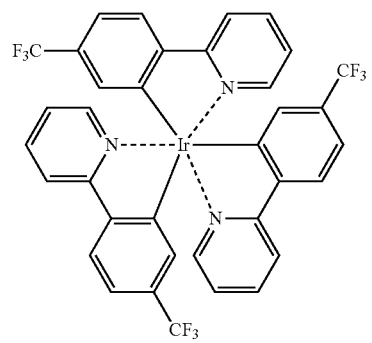
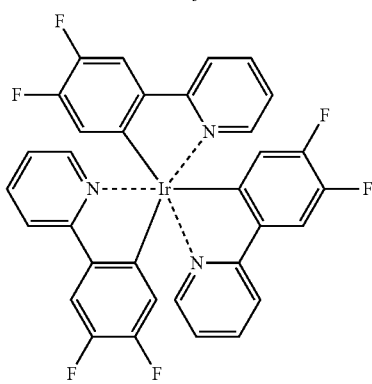
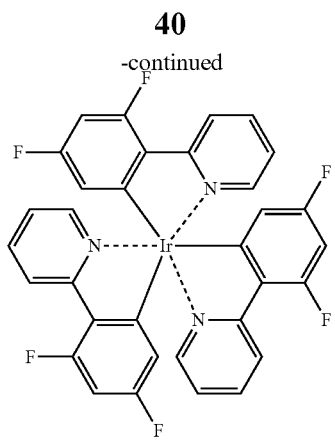
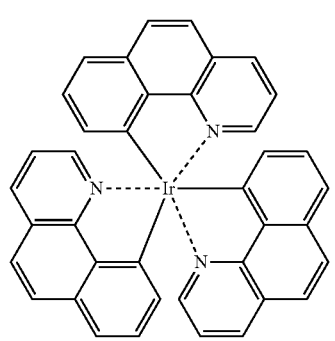
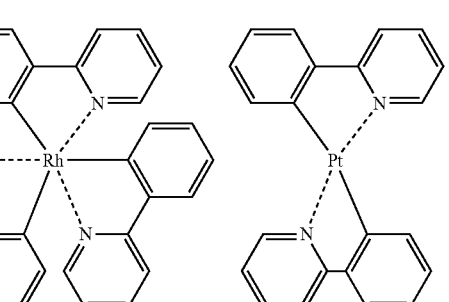
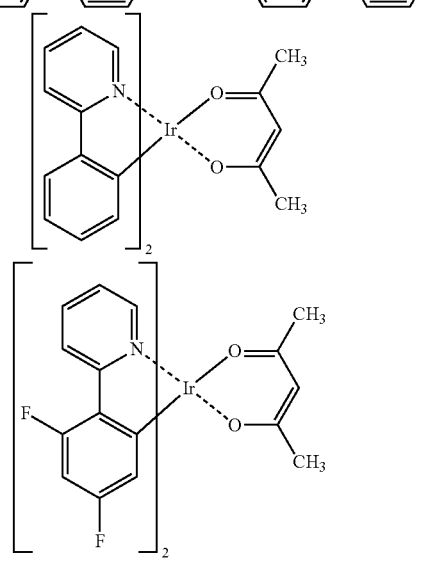

-continued
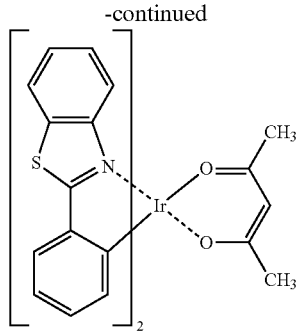
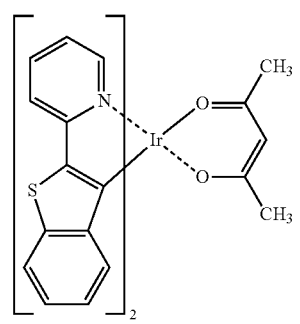
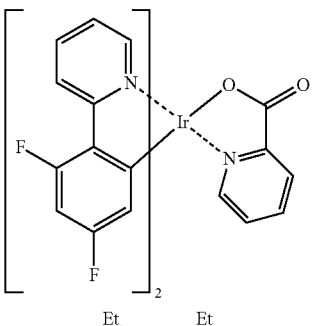
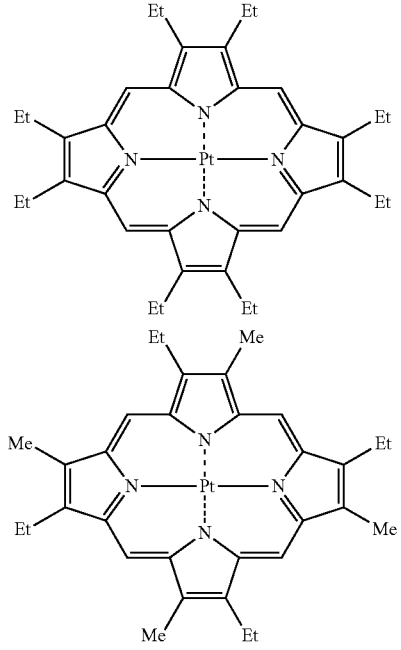
-continued
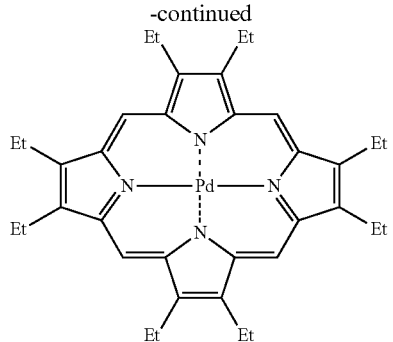
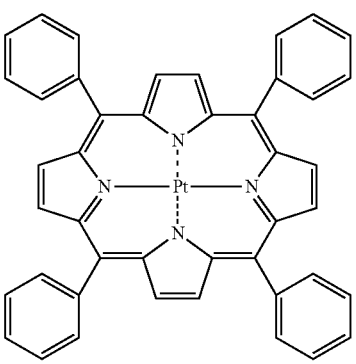
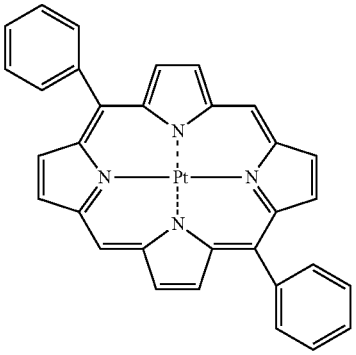
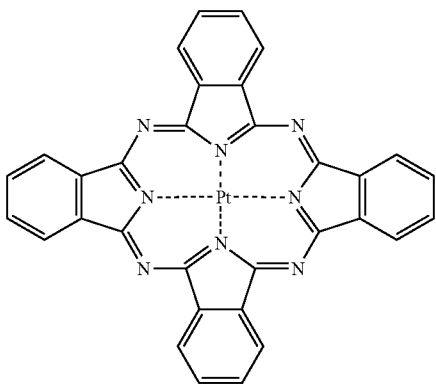

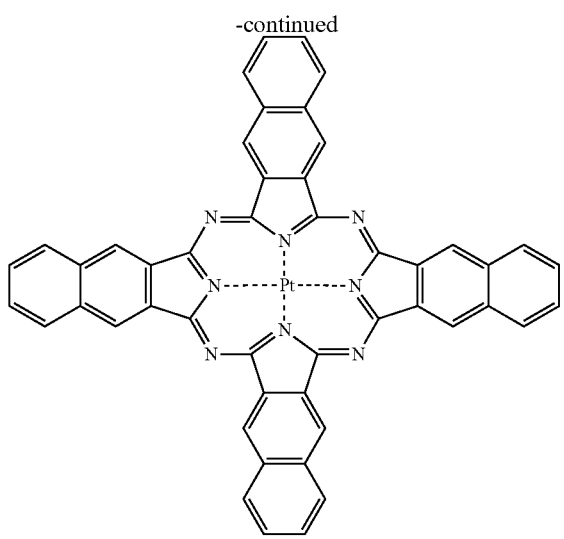

The content of the phosphorescent light-emitting dopant in the light-emitting layer is in the range of preferably 1 to 50 wt %, more preferably 5 to 30 wt %.

It is preferred to use, as a host material in the light-emitting layer, the nitrogen-containing aromatic compound represented by the general formula (1). However, when the nitrogen-containing aromatic compound is used in any of the organic layers other than the light-emitting layer, the material to be used in the light-emitting layer may be any other host material except the nitrogen-containing aromatic compound represented by the general formula (1), or the nitrogen-containing aromatic compound represented by the general formula (1) and any other host material may be used in combination. Further, a plurality of kinds of known host materials may be used in combination.

It is preferred to use, as a known host compound that may be used, a compound that has a hole-transporting ability and an electron-transporting ability, is capable of preventing luminescence from having a longer wavelength, and has a higher glass transition temperature.

Such other host materials are known by many patent literatures and the like, and hence the other host material may be chosen therefrom. Specific examples of the host material include, but not particularly limited to, an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a poly-phenylene derivative, a polyphenylene vinylene derivative, and a polyfluorene derivative.

—Injecting Layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be provided as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the compound of the present invention represented by the general formula (1) for the hole-blocking layer. However, when the compound is used in any other organic layer, a known material for a hole-blocking layer may be used. Further, it is possible to use, as a material for the hole-blocking layer, any of the materials for the electron-transporting layer to be described later as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Although the compound of the present invention represented by the general formula (1) is preferably used as a material for the electron-blocking layer, any of the materials for the hole-transporting layer to be described below can be used as required. The thickness of the electron-blocking layer is preferably 3 to 100 nm, more preferably 5 to 30 nm.

—Exciton-Blocking Layer—

The exciton-blocking layer refers to a layer for blocking excitons produced by the recombination of a hole and an electron in the light-emitting layer from diffusing in charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

A material for the exciton-blocking layer is exemplified by 1,3-dicarbazolylbenzene (mCP) and bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be provided.

The hole-transporting material has hole-injecting property or hole-transporting property or has electron-blocking property, and may be any of an organic compound and an inorganic compound. It is preferred to use the compound of the present invention represented by the general formula (1) as a known hole-transporting material that may be used. However, it is possible to select and use any compound from conventionally known compounds. Examples thereof include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive polymeric oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be provided.

An electron-transporting material (which also serves as a hole-blocking material in some cases) has only to have a function of transferring electrons injected from the cathode into the light-emitting layer. It is preferred to use the compound of the present invention represented by the general formula (1) for the electron-transporting layer. However, it is possible to select and use any compound from conventionally known compounds. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative having a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples. It should be appreciated that the present invention is not limited to Examples below and may be carried out in various forms as long as the various forms do not deviate from the gist of the present invention.

Example 1

Synthesis of Compound (1-1)

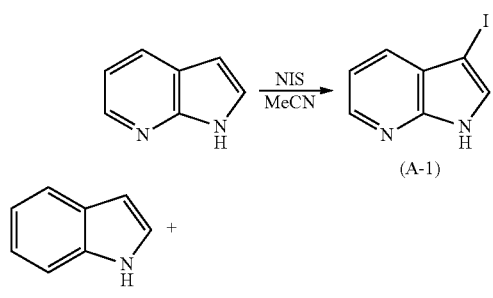

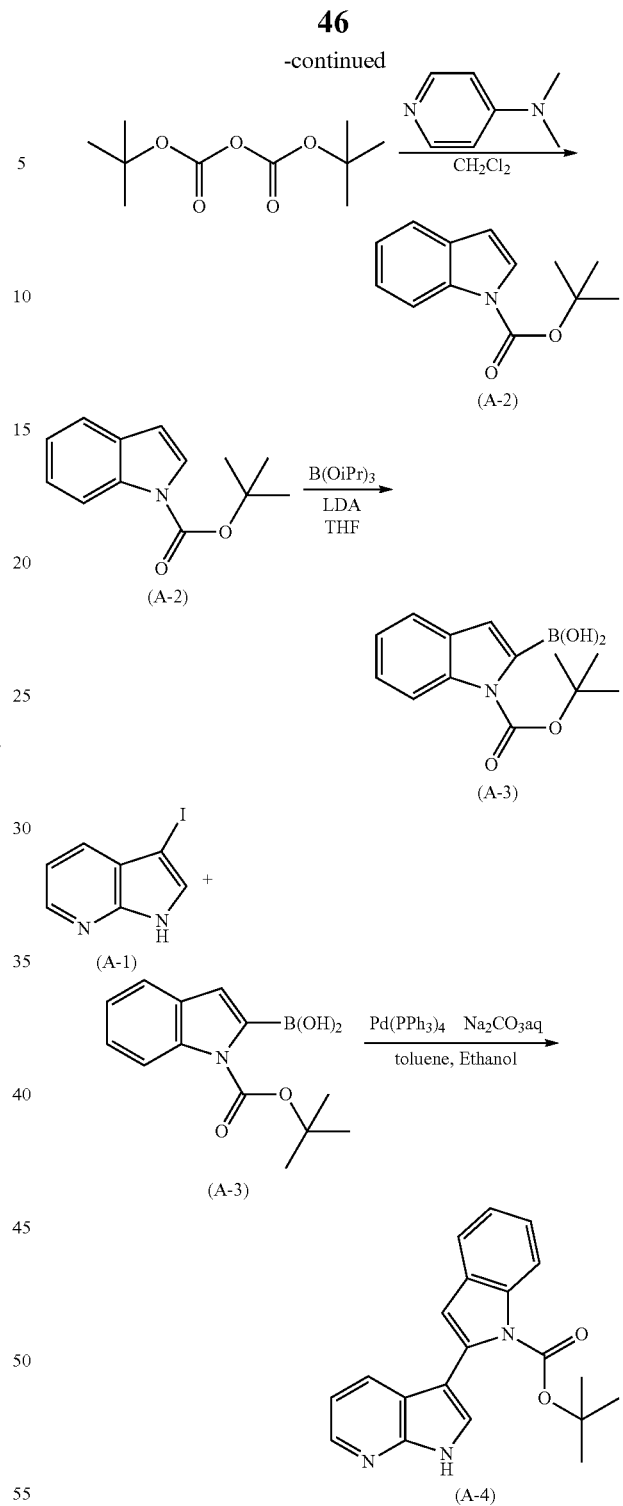

Under an air atmosphere, 11.9 g (101 mmol) of 7-azaindole and 67 ml of acetonitrile (MeCN) were loaded and the mixture was stirred at 50° C. for 5 min. To the resultant solution were added 25.0 g (111 mmol) of N-iodosuccinimide (NIS) and the mixture was stirred at 50° C. for 2 hr. The resultant suspension was filtered and the precipitated crystal was collected by filtration. The crystal was reslurried with 150 ml of water and subsequently with 150 mL of MeCN to give 22.7 g (101 mmol, yield: 100 mol %) of an intermediate (A-1).

Under an air atmosphere, 100 g (854 mmol) of indole, 203 g (931 mmol) of t-butyl dicarbonate (Boc₂O), 1,600 ml of dichloromethane (CH₂Cl₂), and 10.4 g (85.1 mmol) of N,N-dimethylaminopyridine (DMAP) were loaded and the mixture was stirred at room temperature for 2 hr and 30 min. To the reaction solution were added 200 ml of 1 N hydrochloric acid, the mixture was stirred, and the aqueous layer was separated from the organic layer. To the organic layer were added 200 ml of brine, the mixture was stirred, and the aqueous layer was separated from the organic layer. The organic layer was dried over anhydrous sodium sulfate. After that, the sodium sulfate was separated by filtration and the solvent was removed by evaporation under reduced pressure. The resultant residue was purified by silica gel column chromatography to give 184 g (847 mmol, yield: 99 mol %) of an intermediate (A-2).

Under a nitrogen atmosphere, 63.3 g (290 mmol) of the intermediate (A-2), 99.6 g (530 mmol) of triisopropyl borate (B(OiPr)₃), and 370 ml of THF were loaded and the mixture was cooled to 0° C. To the resultant solution were added dropwise 185 ml (2.0 mol/l) of a solution of lithium diisopropyl amide (LDA) in THF. The reaction solution was returned to room temperature and stirred for 2 hr. After that, to the resultant solution were added 370 ml of 2 N hydrochloric acid and the aqueous layer was separated from the organic layer. The aqueous layer was extracted with THF (300 ml) and the combined organic layer was dried over anhydrous magnesium sulfate. The magnesium sulfate was separated by filtration and the solvent was removed by evaporation under reduced pressure to give 74.0 g (283 mmol, yield: 98 mol %) of an intermediate (A-3).

68.4 g (280 mmol) of the intermediate (A-1), 73.0 g (280 mmol) of the intermediate (A-3), 15.6 g (13.5 mmol) of tetrakis(triphenylphosphine)palladium(0) (Pd(PPh₃)₄), a solution of 75.3 g of sodium carbonate (Na₂CO₃) in water (280 ml), 960 ml of toluene, and 510 ml of ethanol were loaded and the mixture was stirred for 4 hr while being heated at 70° C. The reaction solution was cooled to room temperature and then the aqueous layer was separated from the organic layer. The aqueous layer was extracted with toluene (350 ml) and the combined organic layer was dried over anhydrous magnesium sulfate. After the organic layer had been dried over anhydrous magnesium sulfate, the magnesium sulfate was separated by filtration and the solvent was removed by evaporation under reduced pressure. The resultant residue was purified by silica gel column chromatography to give 78.7 g (236 mmol, yield: 84 mol %) of an intermediate (A-4).

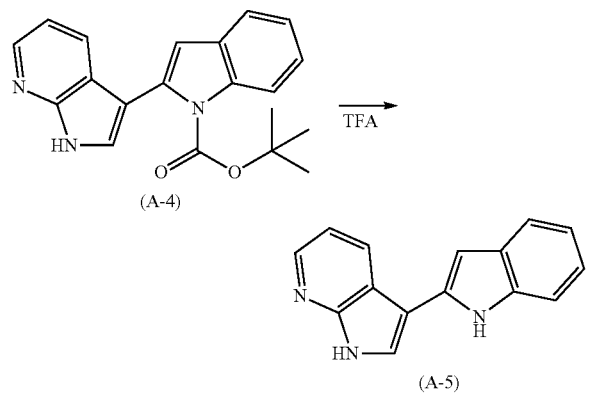

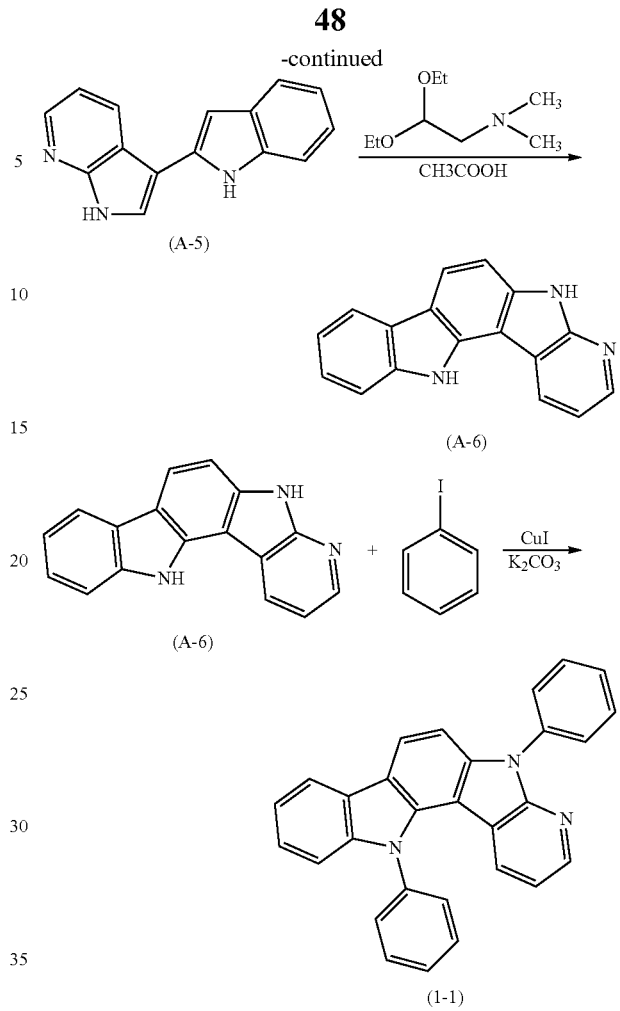

38.7 g (116 mmol) of the intermediate (A-4) and 100 ml of trifluoroacetic acid (TFA) were loaded and the mixture was stirred at room temperature for 2 hr and 30 min. TFA was removed by evaporation under reduced pressure. The resultant residue was purified by silica gel column chromatography to give 26.0 g (111 mol, yield: 96 mol %) of an intermediate (A-5).

26.0 g (111 mmol) of the intermediate (A-5), 22.5 g (139 mmol) of (dimethylamino)acetaldehyde diethylacetal, and 50 ml of acetic acid were loaded and the mixture was stirred for 16 hr while being heated at 140° C. The reaction solution was cooled to room temperature and then the solvent was removed by evaporation under reduced pressure. The resultant residue was purified by silica gel column chromatography to give 15.9 g (61.8 mmol, yield: 55 mol %) of an intermediate (A-6).

APCI-TOFMS, m/z 257 [M+H]⁺

Under a nitrogen atmosphere, 3.6 g (13.9 mmol) of the intermediate (A-6), 130 g (634 mmol) of iodobenzene, 8.5 g (44.5 mmol) of copper iodide, and 12.2 g (88.5 mmol) of potassium carbonate were loaded and the mixture was stirred for 17 hr while being heated at 210° C. After the reaction solution had been cooled to room temperature, Celite 545 was added, the mixture was filtered, and iodobenzene was removed by evaporation under reduced pressure. The resultant residue was purified by silica gel column chromatography to give 3.3 g (8.1 mmol, yield: 59 mol %) of a compound (1-1) as a white solid.

APCI-TOFMS, m/z 410 [M+H]+

¹H-NMR (DMSO-d6): 8.39 (d, J=8.8 Hz, 1H), 8.25-8.27 (m, 1H), 8.23 (dd, J=4.6, 1.5 Hz, 1H), 7.63-7.79 (m, 9H), 7.54-7.59 (m, 1H), 7.31-7.41 (m, 3H), 7.24 (d, J=7.8 Hz, 1H), 6.84 (dd, J=8.1, 4.6 Hz, 1H), 5.92 (dd, J=8.1, 1.5 Hz, 1H)

Example 2

Synthesis of Compound (1-33)

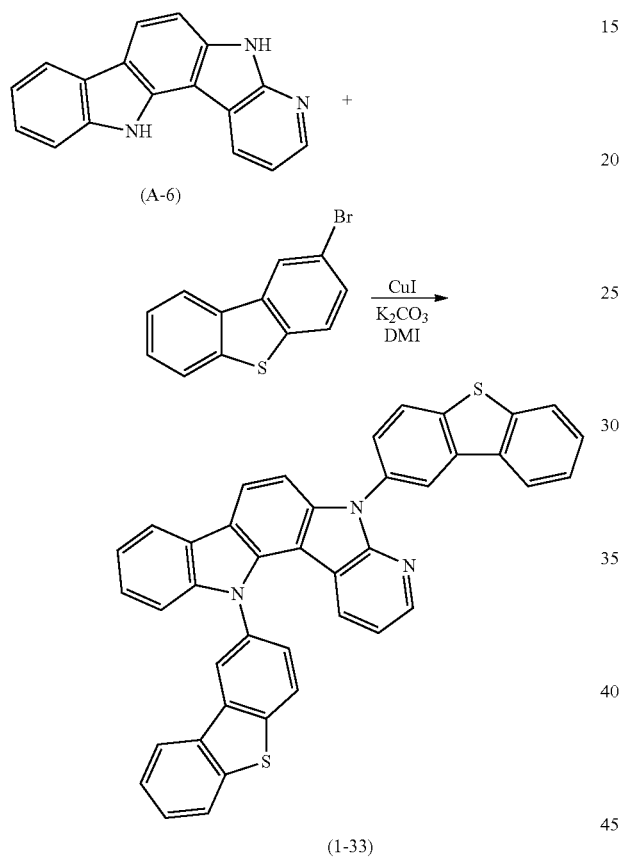

(1-33)

Under a nitrogen atmosphere, 5.5 g (22 mmol) of the intermediate (A-6), 17 g (65 mmol) of 2-bromodibenzobenzene, 100 ml of 1,3-dimethyl-2-imidazolidine (DMI), 16 g (82 mmol) of copper iodide, and 20 g (150 mmol) of potassium carbonate were loaded and the mixture was stirred for 24 hr while being heated at 210° C. After the reaction solution had been cooled to room temperature, Celite 545 was added, the mixture was filtered, and iodobenzene was removed by evaporation under reduced pressure. The resultant residue was purified by silica gel column chromatography to give 8.5 g (14 mmol, yield: 62 mol %) of a compound (1-33) as a white solid.

APCI-TOFMS, m/z 622 [M+H]+

1H-NMR (DMSO-d6): δ 8.86 (d, J=2.0 Hz, 1H), 8.67 (d, J=2.2 Hz, 1H), 8.42-8.67 (m, 4H), 8.31 (d, J=8.5 Hz, 1H), 8.29 (d, J=8.1 Hz, 1H), 8.10-8.17 (m, 3H), 7.84 (dd, J=8.3, 2.2 Hz, 1H), 7.74 (dd, J=8.3, 2.2 Hz, 1H), 7.55-7.62 (m, 2H), 7.47-7.52 (m, 2H), 7.32-7.39 (m, 4H), 6.38 (dd, J=8.1, 4.9 Hz, 1H), 5.94 (dd, J=8.1, 1.4 Hz, 1H)

Example 3

Synthesis of Compound (1-46)

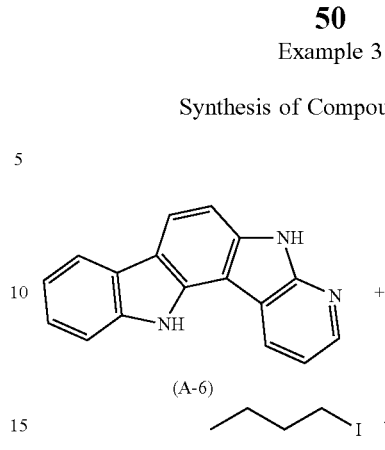

(1-46)

Under a nitrogen atmosphere, 2.7 g (68 mmol) of sodium hydride (60.5% product) and 20 ml of DMF were loaded and the mixture was stirred at room temperature for 0.5 hr. To the resultant suspension was added a solution of 7.0 g (27 mmol) of the intermediate (A-6) in DMF (200 ml) and the mixture was stirred at room temperature for 30 min. To the resultant suspension were added 20 g (110 mmol) of iodobutane and the mixture was stirred at 130° C. for 20 hr. To the stirred reaction solution was added distilled water (700 ml) and the precipitated solid was collected by filtration. The resultant solid was purified by reslurrying to give 6.3 g (17 mmol, yield: 64 mol %) of a compound (1-46) as a white solid.

APCI-TOFMS, m/z 370 [M+H]+

¹H-NMR (DMSO-d6): δ 8.86 (dd, J=8.1, 1.2 Hz, 1H), 8.50 (dd, J=4.6, 1.2 Hz, 1H), 8.36 (d, J=8.5 Hz, 1H), 8.18 (d, J=7.6 Hz, 1H), 7.73 (d, J=8.3 Hz, 1H), 7.57 (d, J=8.5 Hz, 1H), 7.41 (dd, J=7.1, 1.2 Hz, 1H), 7.35 (dd, J=8.0, 4.6 Hz, 1H), 7.24 (t, J=7.0 Hz, 1H), 4.93 (t, J=7.3 Hz, 2H), 4.62 (t, J=7.3 Hz, 2H), 1.80-1.94 (m, 4H), 1.33-1.41 (m, 4H), 0.91 (t, J=7.3 Hz, 3H), 0.84 (t, J=7.3 Hz, 3H)

Example 4

On a glass substrate on which an anode made of ITO and having a thickness of 110 nm had been formed, poly(3,4-ethylenedioxythiophene)/polystyrenesulfonic acid (PEDOT/PSS): (manufactured by H.C. Starck Ltd., trade name: Clevios PCH8000) was formed into a film having a thickness of 25 nm on the ITO by a spin coating method. Next, 4,4'-bis[N-(1-naphthyl)-N-phenylamino]biphenyl (NPB) was formed into a film having a thickness of 40 nm to serve as a hole-transporting layer by a vacuum deposition method at a degree of vacuum of $4.0 \times 10^{-5}$ Pa. Next, the compound (1-1) obtained in Synthesis Example 1 as a host material and tris(2-phenylpyridine)iridium(III) (Ir(ppy)₃) as a phosphorescent light-emitting dopant were co-deposited from different deposition sources onto the hole-transporting layer to form a film having a thickness of 40 nm to serve as a light-emitting layer. The concentration of Ir(ppy)$_3$ in the light-emitting layer was 6.0 wt %. Next, tris(8-hydroxyquinolinato)aluminum(III) (Alq3) was formed into a film having a thickness of 20 nm to serve as an electron-transporting layer. Further, lithium fluoride (LiF) was formed into a film having a thickness of 1.0 nm to serve as an electron-injecting layer on the electron-transporting layer. Finally, aluminum (Al) was formed into a film having a thickness of 130 nm to serve as an electrode on the electron-injecting layer. Thus, an organic EL device was produced.

The resultant organic EL device was measured for the following initial characteristics: luminance (cd/m$^2$), voltage (V), and visual luminous efficiency (lm/W) in the case of connecting the device to an external power source and applying a DC voltage to the device so that the current density reached 100 mA/cm$^2$. An organic EL device obtained in each of Examples and Comparative Examples shown below was also measured in the same manner as described above. Table 1 shows the results. It should be noted that it was found that the local maximum wavelength of the emission spectrum of the device was 530 nm and hence light emission from Ir(ppy)$_3$ was obtained.

Example 5

An organic EL device was produced in the same manner as in Example 4 except that the compound (1-33) was used as the host material for the light-emitting layer.

Example 6

An organic EL device was produced in the same manner as in Example 4 except that the compound (1-46) was used as the host material for the light-emitting layer.

Comparative Example 1

An organic EL device was produced in the same manner as in Example 4 except that the following compound (H-1) was used as the host material for the light-emitting layer.

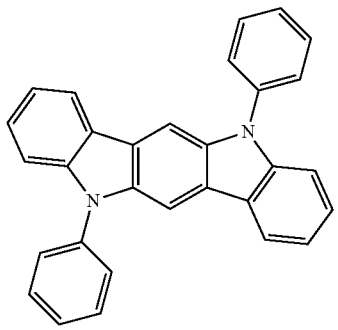

(H-1)

Comparative Example 2

An organic EL device was produced in the same manner as in Example 4 except that the following compound (H-2) was used as the host material for the light-emitting layer.

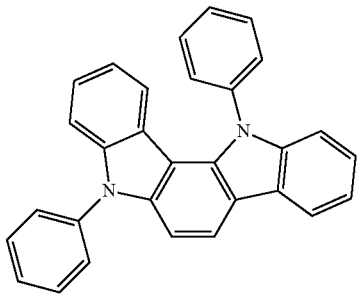

(H-2)

Comparative Example 3

An organic EL device was produced in the same manner as in Example 4 except that the following compound TAZ was used as the host material for the light-emitting layer.

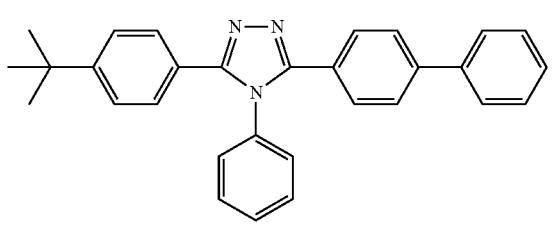

TAZ

It was found that the local maximum wavelength of the emission spectrum of each of the organic EL devices produced in Examples 5 and 6 was 530 nm, and hence light emission from Ir(ppy)$_3$ was obtained.

TABLE 1

| | Host material compound | Luminance (cd/m$^2$) | Voltage (V) | Visual luminous efficiency (lm/W) |
|---|---|---|---|---|
| Example 4 | 1-1 | 7,700 | 9.7 | 2.5 |
| 5 | 1-33 | 11,540 | 8.5 | 3.8 |
| 6 | 1-46 | 7,310 | 9.2 | 2.4 |
| Comparative Example 1 | H-1 | 1,100 | 5.1 | 0.6 |
| 2 | H-2 | 1,500 | 8.8 | 0.5 |
| 3 | TAZ | 900 | 12.4 | 0.2 |

Example 7

On a glass substrate on which an anode made of ITO and having a thickness of 110 nm had been formed, poly(3,4-ethylenedioxythiophene)/polystyrenesulfonic acid (PEDOT/PSS) (manufactured by H.C. Starck Ltd., trade name: Clevios PCH8000) was formed into a film having a thickness of 25 nm on the ITO by a spin coating method. Next, a 0.4 wt % solution of the compound (1-1) as a hole-transporting material (HTM) was prepared by dissolving the compound in tetrahydrofuran and formed into a film having a thickness of 20 nm to serve as a hole-transporting layer by the spin coating method. Next, 4,4'-bis(9-carbazolyl)biphenyl (CBP) as a host material and Ir(ppy)$_3$ as a phosphorescent light-emitting dopant were co-deposited from different deposition sources by a vacuum deposition method at a degree of vacuum of 4.0×10⁻⁵ Pa to form a film having a thickness of 50 nm to serve as a light-emitting layer. The concentration of Ir(ppy)₃ in the light-emitting layer was 10.0 wt %. Next, Alq3 was formed into a film having a thickness of 30 nm to serve as an electron-transporting layer. Further, LiF was formed into a film having a thickness of 0.5 nm on the electron-transporting layer to serve as an electron-injecting layer. Finally, Al was formed into a film having a thickness of 150 nm on the electron-injecting layer to serve as an electrode. Thus, an organic EL device was produced.

The resultant organic EL device was measured for the following initial characteristics: luminance (cd/m²), voltage (V), and visual luminous efficiency (lm/W) in the case of connecting the device to an external power source and applying a DC voltage to the device so that the current density reached 100 mA/cm². An organic EL device obtained in each of Examples and Comparative Example shown below was also measured in the same manner as described above. Table 2 shows the results.

Example 8

An organic EL device was produced in the same manner as in Example 7 except that the compound (1-33) was used as the hole-transporting material.

Example 9

An organic EL device was produced in the same manner as in Example 7 except that the compound (1-46) was used as the hole-transporting material.

Comparative Example 4

An organic EL device was produced in the same manner as in Example 7 except that the compound (H-1) was used for the hole-transporting layer.

It was found that the local maximum wavelength of the emission spectrum of each of the organic EL devices produced in Examples 7 to 9 was 530 nm, and hence light emission from Ir(ppy)₃ was obtained. Table 2 shows the results. HTM stands for hole-transporting material.

TABLE 2

| | HTM compound | Luminance (cd/m²) | Voltage (V) | Visual luminous efficiency (lm/W) |
|---|---|---|---|---|
| Example 7 | 1-1 | 20,170 | 14.8 | 4.2 |
| 8 | 1-33 | 29,250 | 8.5 | 6.3 |
| 9 | 1-46 | 18,100 | 14.1 | 4.0 |
| Comparative Example 4 | H-1 | 12,860 | 15.6 | 3.9 |

Example 10

Synthesis of Compound (2-1)

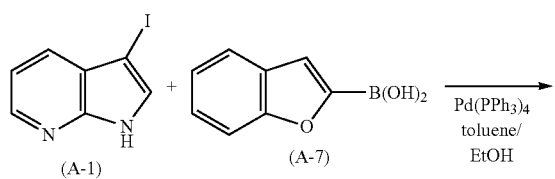

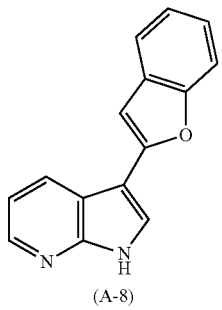

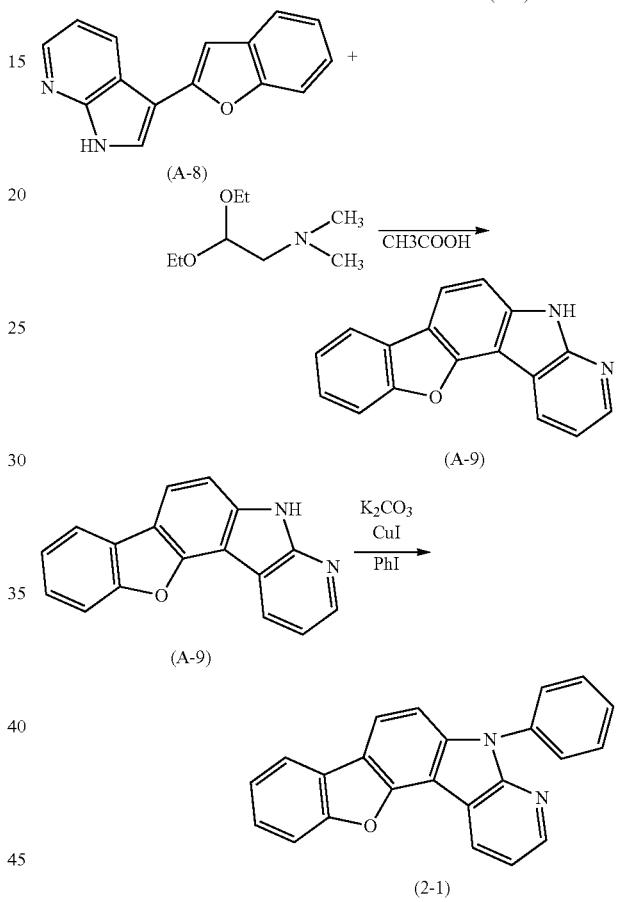

75.9 g (310 mmol) of the intermediate (A-1), 50.0 g (30.9 mmol) of benzofuran-2-boronic acid (A-7), 4.3 g (3.8 mmol) of tetrakis(triphenylphosphine)palladium(0) (Pd(PPh₃)₄), 390 ml of a 2 N aqueous solution of sodium carbonate (Na₂CO₃), 815 ml of toluene, and 490 ml of ethanol were loaded and the mixture was stirred for 21 hr while being heated at 70° C. The reaction solution was cooled to room temperature and then the aqueous layer was separated from the organic layer. The aqueous layer was extracted with toluene (350 ml) and the combined organic layer was dried over anhydrous magnesium sulfate. After the organic layer had been dried over anhydrous magnesium sulfate, the magnesium sulfate was separated by filtration and the solvent was removed by evaporation under reduced pressure. The resultant residue was purified by silica gel column chromatography to give 14.1 g (60 mmol, yield: 19%) of an intermediate (A-8).

APCI-TOFMS, m/z 235 [M+H]⁺

5.0 g (20.0 mmol) of the intermediate (A-8), 5.2 g (32.1 mmol) of (dimethylamino)acetaldehyde diethylacetal, and 65 ml of acetic acid were loaded and the mixture was stirred for 96 hr while being heated at 140° C. The reaction solution was cooled to room temperature and then the solvent was removed by evaporation under reduced pressure. The resultant residue was purified by silica gel column chromatography to give 1.3 g (4.9 mmol, yield: 25 mol %) of an intermediate (A-9).

FD-MS, m/z 258 [M]

Under a nitrogen atmosphere, 1.3 g (13.9 mmol) of the intermediate (A-9), 32 g (156 mmol) of iodobenzene, 2.0 g (10.7 mmol) of copper iodide, and 2.9 g (21.1 mmol) of potassium carbonate were loaded and the mixture was stirred for 24 hr while being heated at 210° C. After the reaction solution had been cooled to room temperature, Celite 545 was added, the mixture was filtered, and iodobenzene was removed by evaporation under reduced pressure. The resultant residue was purified by silica gel column chromatography to give 1.3 g (3.7 mmol, yield: 73 mol %) of a compound (2-1) as a solid.

FD-MS, m/z 334 [M]

$^1$H-NMR (DMSO-d6): 8.63 (d, J=8.8 Hz, 1H), 8.51-8.53 (m, 1H), 8.22 (d, J=8.0 Hz, 1H), 7.82 (d, J=8.0 Hz, 1H), 7.48-7.80 (m, 6H), 7.20-7.45 (m, 4H)

Example 11

Synthesis of Compound (3-1)

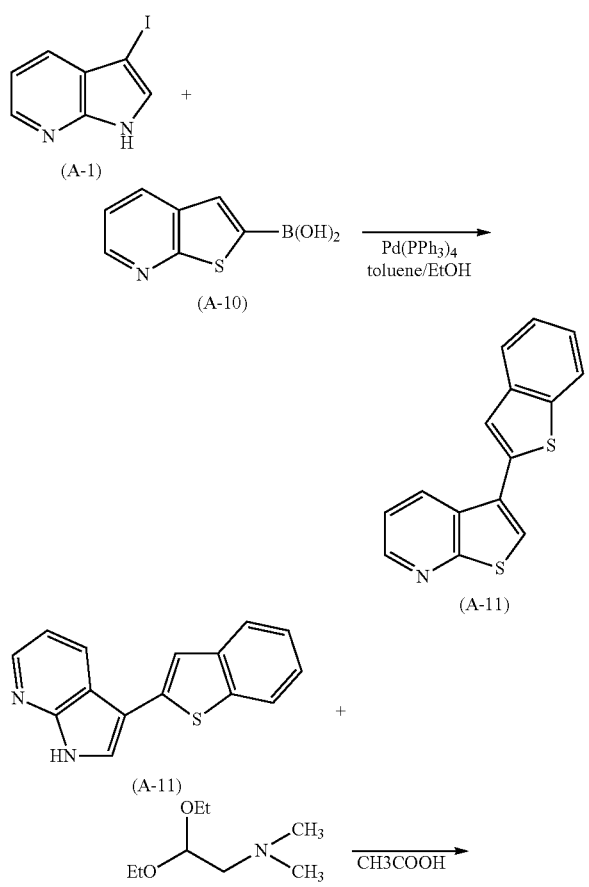

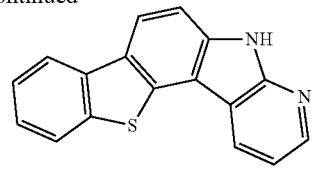

(A-12)

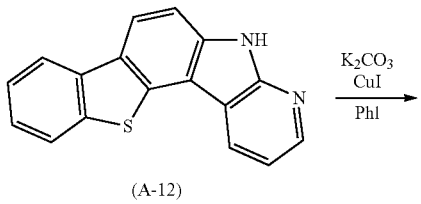

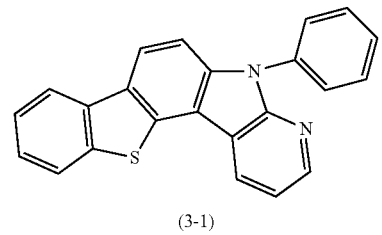

(3-1)

69.7 g (286 mmol) of the intermediate (A-1), 50.5 g (284 mmol) of benzothiophene-2-boronic acid (A-10), 5.3 g (4.6 mmol) of tetrakis(triphenylphosphine)palladium(0) (Pd (PPh$_3$)$_4$), 360 ml of a 2 N aqueous solution of sodium carbonate (Na$_2$CO$_3$), 815 ml of toluene, and 490 ml of ethanol were loaded and the mixture was stirred for 22 hr while being heated at 70° C. The reaction solution was cooled to room temperature and then the aqueous layer was separated from the organic layer. The aqueous layer was extracted with toluene (350 ml) and the combined organic layer was dried over anhydrous magnesium sulfate. After the organic layer had been dried over anhydrous magnesium sulfate, the magnesium sulfate was separated by filtration and the solvent was removed by evaporation under reduced pressure. The resultant residue was purified by silica gel column chromatography to give 10.3 g (41 mmol, yield: 14 mol %) of an intermediate (A-11).

APCI-TOFMS, m/z 251 [M+H]$^+$ 5.0 g (20.0 mmol) of the intermediate (A-11), 4.8 g (30.0 mmol) of (dimethylamino)acetaldehyde diethylacetal, and 78 ml of acetic acid were loaded and the mixture was stirred for 96 hr while being heated at 140° C. The reaction solution was cooled to room temperature and then the solvent was removed by evaporation under reduced pressure. The resultant residue was purified by silica gel column chromatography to give 2.3 g (8.4 mmol, yield: 42 mol %) of an intermediate (A-12).

FD-MS, m/z 274 [M]

Under a nitrogen atmosphere, 2.3 g (8.4 mmol) of the intermediate (A-12), 53 g (260 mmol) of iodobenzene, 3.4 g (17.8 mmol) of copper iodide, and 4.9 g (35.2 mmol) of potassium carbonate were loaded and the mixture was stirred for 24 hr while being heated at 210° C. After the reaction solution had been cooled to room temperature, Celite 545 was added, the mixture was filtered, and iodobenzene was removed by evaporation under reduced pressure. The resultant residue was purified by silica gel column chromatography to give 1.9 g (5.5 mmol, yield: 65 mol %) of a compound (3-1) as a solid.

FD-MS, m/z 350 [M+H]$^+$

1H-NMR (DMSO-d6): 8.53 (d, J=8.2 Hz, 1H), 8.47-8.50 (m, 1H), 8.16 (d, J=8.0 Hz, 1H), 7.84 (d, J=8.0 Hz, 1H), 7.45-7.78 (m, 6H), 7.21-7.43 (m, 4H)

Example 12

An organic EL device was produced in the same manner as in Example 4 except that the compound (2-1) was used as the host material for the light-emitting layer.

Example 13

An organic EL device was produced in the same manner as in Example 4 except that the compound (3-1) was used as the host material for the light-emitting layer.

The devices were evaluated in the same manner as in Example 4. It was found that the local maximum wavelength of the emission spectrum of each of the devices produced in Examples 12 and 13 was 530 nm, and hence light emission from Ir(ppy)$_3$ was obtained. Table 3 shows the light-emitting characteristics.

TABLE 3

|  | Host material compound | Luminance (cd/m²) | Voltage (V) | Visual luminous efficiency (lm/W) |
|---|---|---|---|---|
| Example 12 | 2-1 | 9,960 | 8.9 | 8.9 |
| 13 | 3-1 | 10,080 | 8.8 | 3.6 |

Example 14

An organic EL device was produced in the same manner as in Example 7 except that the compound (2-1) was used as the hole-transporting material.

Example 15

An organic EL device was produced in the same manner as in Example 7 except that the compound (3-1) was used as the hole-transporting material.

The devices were evaluated in the same manner as in Example 7. It was found that the local maximum wavelength of the emission spectrum of each of the devices produced in Examples 14 and 15 was 530 nm, and hence light emission from Ir(ppy)$_3$ was obtained. Table 4 shows the light-emitting characteristics.

TABLE 4

|  | HTM compound | Luminance (cd/m2) | Voltage (V) | Visual luminous efficiency (lm/W) |
|---|---|---|---|---|
| Example 14 | 2-1 | 24,200 | 14.7 | 5.0 |
| 15 | 3-1 | 25,210 | 14.5 | 5.3 |

INDUSTRIAL APPLICABILITY

The skeleton of the nitrogen-containing aromatic compound of the present invention is expected to improve charge transfer by virtue of a lone pair on a nitrogen atom in a terminal heterocycle of the compound. In addition, the skeleton is estimated to enable the control of various energy values, i.e., an ionization potential, an electron affinity, and triplet excitation energy by virtue of the terminal heterocycle and a substituent on nitrogen. The organic EL device using the skeleton can be expected to have improved efficiency by virtue of excellent charge transfer. In addition, the skeleton exhibits a satisfactory amorphous characteristic and high thermal stability and is electrochemically stable, and hence is estimated to achieve an organic EL device having long driving lifetime and high durability.

The organic EL device according to the present invention has light-emitting characteristics, driving lifetime, and durability at practically satisfactory levels. Thus, the organic EL device has a large technical value in applications to flat panel displays (display devices for portable phones, in-vehicle display devices, display devices for OA computers, televisions, and the like), light sources exerting characteristics of planar light emitters (light sources in lighting equipment and copiers and backlight sources in liquid crystal displays and instruments), sign boards, sign lamps, and the like.

The invention claimed is:

1. A nitrogen-containing aromatic compound, which is represented by the general formula (2):

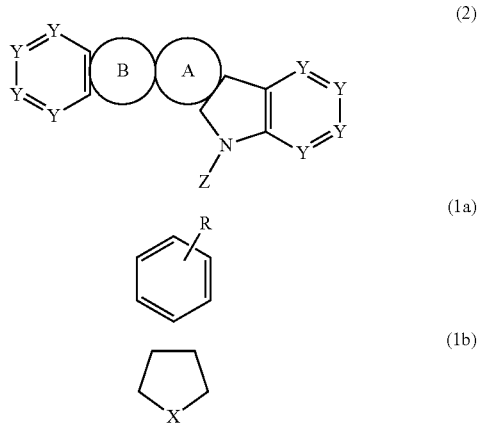

in the formula (2):

ring A represents an aromatic ring represented by the formula (1a) and fused with two adjacent rings at arbitrary positions;

ring B represents a heterocycle represented by the formula (1b) and fused with two adjacent rings at arbitrary positions;

Y's each represent C—R or N, provided that one to four of Y's each represent N;

X's each represent N—Z;

R represents hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 50 carbon atoms, or an aromatic heterocyclic group having 3 to 50 carbon atoms and free of a fused heterocycle having four or more rings; and Z represents a monovalent group produced by removing hydrogen from dibenzofuran or dibenzothiophene, wherein the dibenzofuran and dibenzothiophene may have a substituent, and the substituent is an alkyl group having 1 to 20 carbon atoms, a cycloalkyl group having 3 to 20 carbon atoms, an alkoxy group having 1 to 20 carbon atoms, an acyl group having 2 to 20 carbon atoms, a dialkylamino group having 2 to 20 carbon atoms, a diarylamino group having 6 to 28 carbon atoms, a phosphanyl group having 6 to 18 carbon atoms, or a silyl group having 3 to 18 carbon atoms.

2. A nitrogen-containing aromatic compound according to claim 1, wherein the nitrogen-containing aromatic compound is the compound 1-33

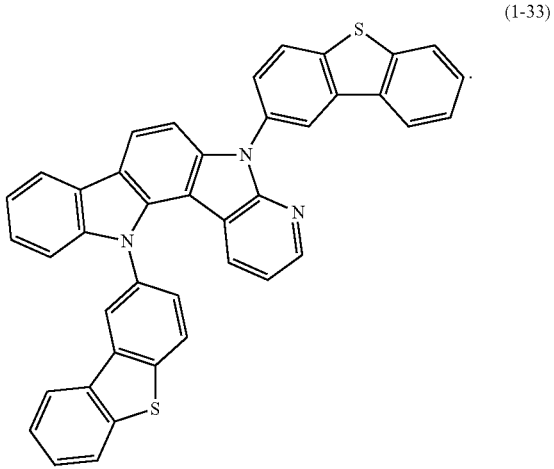 [SMILES: c1ccc2c(c1)sc1ccc(-n3c4ccc5c6ccccc6n(-c6ccc7sc8ccccc8c7c6)c5c4c4cccnc43)cc12]

(1-33)

3. A nitrogen-containing aromatic compound according to claim 1, wherein one or two of Y's in the general formula (2) each represent N.

4. An organic electroluminescent device, comprising the nitrogen-containing aromatic compound according to claim 1.

5. An organic electroluminescent device according to claim 4, wherein an organic layer that contains the nitrogen-containing aromatic compound comprises at least one layer selected from a light-emitting layer, a hole-transporting layer, an electron-transporting layer, and a hole-blocking layer.

6. An organic electroluminescent device according to claim 4, wherein an organic layer that contains the nitrogen-containing aromatic compound is a light-emitting layer or a hole-transporting layer.

7. An organic electroluminescent device according to claim 4, wherein an organic layer that contains the nitrogen-containing aromatic compound comprises a light-emitting layer of an organic electroluminescent device including the light-emitting layer between an anode and a cathode laminated on a substrate, and the light-emitting layer contains a phosphorescent light-emitting dopant and the nitrogen-containing aromatic compound as a host material.

8. An organic electroluminescent device, comprising the nitrogen-containing aromatic compound according to claim 2.

* * * * *